US006893877B2

(12) United States Patent
Hunter et al.

(10) Patent No.: US 6,893,877 B2
(45) Date of Patent: May 17, 2005

(54) METHODS FOR SCREENING SUBSTANCES IN A MICROWELL ARRAY

(75) Inventors: Ian Hunter, Lincoln, MA (US); Colin J. H. Brenan, Marblehead, MA (US); Tanya S. Kanigan, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 301 days.

(21) Appl. No.: 09/850,123

(22) Filed: May 7, 2001

(65) Prior Publication Data
US 2002/0001546 A1 Jan. 3, 2002

Related U.S. Application Data

(63) Continuation-in-part of application No. 09/225,583, filed on Jan. 5, 1999, now Pat. No. 6,387,331.
(60) Provisional application No. 60/071,179, filed on Jan. 12, 1998, and provisional application No. 60/239,538, filed on Oct. 10, 2000.

(51) Int. Cl.[7] .......................... G01N 1/10; G01N 21/03
(52) U.S. Cl. ...................... 436/174; 356/244; 356/246; 362/355; 422/56; 422/82.09; 422/102; 436/165; 436/179; 436/180
(58) Field of Search .......................... 422/56, 58, 100, 422/82.05, 102, 82.09, 104; 356/244, 246; 436/165, 174, 179–180; 359/599, 886; 362/318, 342, 354–356

(56) References Cited

U.S. PATENT DOCUMENTS

| | | | | |
|---|---|---|---|---|
| 1,236,137 A | * | 8/1917 | Bastow | .......................... 362/355 |
| 2,745,001 A | * | 5/1956 | Guth | .......................... 362/354 |
| 3,170,980 A | * | 2/1965 | Pritchard | .................... 385/133 |
| 3,864,512 A | | 2/1975 | Ohno | .......................... 118/637 |
| 3,873,268 A | | 3/1975 | McKie | .......................... 23/230 |
| 4,110,165 A | * | 8/1978 | Cole et al. | .................... 435/119 |
| 4,111,754 A | | 9/1978 | Park | .......................... 195/127 |
| 4,446,239 A | | 5/1984 | Tsuji | .......................... 436/532 |
| 4,493,815 A | | 1/1985 | Fernwood et al. | .......... 422/101 |
| 4,562,045 A | | 12/1985 | Murata | ...................... 422/102 |
| 4,682,890 A | | 7/1987 | de Macario et al. | ........ 356/244 |
| 4,828,386 A | | 5/1989 | Matkovich et al. | ......... 256/246 |
| 4,834,946 A | | 5/1989 | Levin | .......................... 422/101 |
| 5,000,921 A | | 3/1991 | Hanaway | .................... 422/100 |
| 5,047,215 A | | 9/1991 | Manns | ....................... 422/101 |

(Continued)

FOREIGN PATENT DOCUMENTS

| | | | |
|---|---|---|---|
| EP | 0 506 993 | 4/1991 | |
| WO | WO 95/01559 | 1/1995 | ............ G01N/1/28 |
| WO | WO 95/11755 | 5/1995 | ............ B01L/3/00 |
| WO | WO 97/15394 | 5/1997 | ............ B01L/3/00 |
| WO | WO 99/39829 | 8/1999 | |
| WO | WO 01/61054 | 8/2001 | |

OTHER PUBLICATIONS

Cadus, Cadus Pharmaceutical Corp, 1997 Annual Report, 1–29, May 8, 1998.

Primary Examiner—Arlen Soderquist
(74) Attorney, Agent, or Firm—Bromberg & Sunstein LLP

(57) ABSTRACT

Methods for manufacturing and using an apparatus for manipulating and analyzing a large number of microscopic samples of a liquid or materials, including cells, in liquid suspension. Parallel through-holes are formed in a platen and loaded with a liquid. Loading may be performed in such a way as to create a gradient, with respect to the position of the through-holes, of the concentration of a particular substance or of another quantity. Mixing of the contents of through-holes may be obtained by bringing filled microwell arrays into contact with each other with registration of individual through-holes.

10 Claims, 27 Drawing Sheets

U.S. PATENT DOCUMENTS

| | | | |
|---|---|---|---|
| 5,108,704 A | 4/1992 | Bowers et al. | 422/70 |
| 5,210,021 A | 5/1993 | Goodwin | 435/29 |
| 5,262,128 A | 11/1993 | Leighton et al. | 422/100 |
| 5,284,753 A | 2/1994 | Goodwin | 435/30 |
| 5,290,705 A | 3/1994 | Davis | 436/164 |
| 5,382,985 A * | 1/1995 | Becker et al. | 359/289 |
| 5,453,252 A | 9/1995 | Truett | 422/104 |
| 5,506,141 A | 4/1996 | Weinreb et al. | 435/309.1 |
| 5,508,200 A | 4/1996 | Tiffany et al. | 436/44 |
| 5,519,218 A | 5/1996 | Chang | 250/339.07 |
| 5,560,811 A | 10/1996 | Briggs et al. | 204/451 |
| 5,770,440 A | 6/1998 | Berndt | 435/288.4 |
| 5,786,226 A | 7/1998 | Böcker et al. | 436/164 |
| 5,843,767 A | 12/1998 | Beattie | 435/287.1 |
| 6,027,873 A | 2/2000 | Schellenberger et al. | 435/4 |
| 6,387,331 B1 * | 5/2002 | Hunter | 422/102 |

* cited by examiner

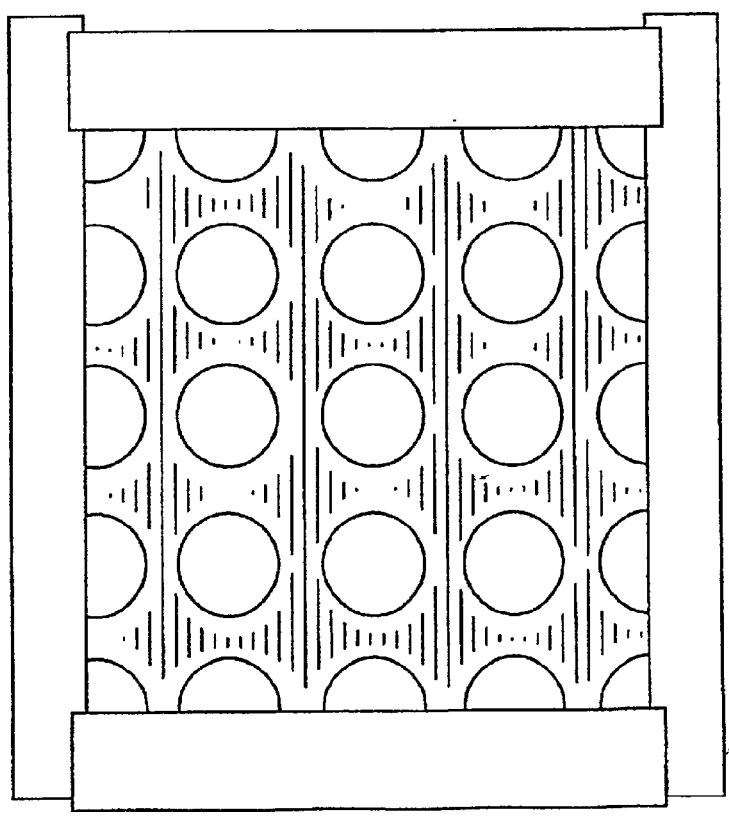
FIG. 2a RECTANGULAR PACKING
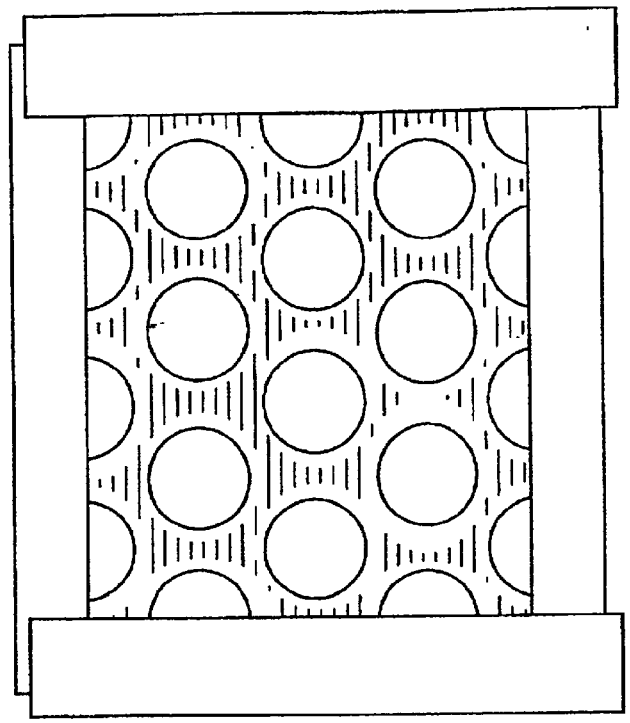
FIG. 2b CLOSE PACKING

METHODS FOR SCREENING SUBSTANCES IN A MICROWELL ARRAY

The present application is a continuation-in-part of U.S. patent application Ser. No. 09/225,583, filed Jan. 5, 1999, issued May 14, 2002 as U.S. Pat. No. 6,387,331, which in turn claims priority from U.S. Provisional Application No. 60/071,179, filed Jan. 12, 1998, both of which applications are herein incorporated by reference. The present application claims priority, additionally, from U.S. Provisional Application No. 60/239,538, filed Oct. 10, 2000, which is also incorporated herein by reference.

FIELD OF THE INVENTION

The present invention pertains to methods for manufacturing and using apparatus for manipulating, transporting, and analyzing a large number of microscopic samples of a liquid or of materials including cells currently or formerly in liquid suspension.

BACKGROUND OF THE INVENTION

Chemistry on the micro-scale, involving the reaction and subsequent analysis of quantities of reagents or analytes of order microliters or smaller, is an increasingly important aspect of the development of new substances in the pharmaceutical and other industries. Such reaction and analysis may accommodate vast libraries containing as many as a million compounds to be reacted and analyzed under various conditions. Significant problems associated with current technologies as applied to chemical analysis of vast numbers (potentially on the order of hundreds of thousands or millions per day) of compounds include the problem of handling vast numbers of compounds and reactions in parallel.

Existing technology relies on 96-, 384-, or 1536-well plates containing quantities between approximately 1 microliter and 1 milliliter of liquid compound per well, and, generally, involves chemical reactions and analysis in wells disposed with single openings on flat surfaces such as polystyrene. It is not practical to apply existing technology in the art to form million-well microtiter plates. There is a need, therefore, for new approaches that permit the analysis of a million samples in a laboratory format.

SUMMARY OF THE INVENTION

In accordance with preferred embodiments of the present invention, a method is provided for loading a plurality of disparate sample containers, the sample containers comprising an integral structure, such that the concentration of a specified substance in each container is characterized by a gradient with respect to position of the container within the structure. The method has the steps of introducing a first liquid into the disparate containers and contacting the containers with a second liquid, the second liquid containing the specified substance, in such a manner that the degree of diffusion of the specified substance into the disparate containers differs in a controlled manner among the containers.

In accordance with alternate embodiments of the invention, the duration of contact with the second liquid may be differed as among the disparate containers. The diffusion rate of the specified substance into the containers may be modulated. The method may have the further step of creating a gradient of the specified substance in the second liquid, and the gradient may be created by applying electrophoresis. The diffusion rate may be modulated by contacting the containers with the second liquid through a membrane with different permeability at different portions of the membrane.

The step of introducing the liquid into containers may include loading the liquid into a plurality of substantially parallel through-holes in a platen. Loading may be performed by forming a droplet of the liquid on the end of a liquid transfer device, moving the fluid transfer device so as to drag the droplet across the top surface of the platen and over the through-holes to be filled, dispensing the liquid to keep the droplet from being depleted, and withdrawing the droplet from the surface after the through-holes are filled.

In accordance with further embodiments of the invention, a method is provided for loading a liquid sample into a plurality of through-holes of a platen. The method has the steps of filling an array of capillary tubes having dispensing ends, disposing each dispensing end in proximity to a distinct through-hole, and transferring liquids to the through-holes of the platen through the capillary tubes. An alternate method has steps of creating regions of distinct concentration of the specified substance in a liquid, such as by electrophoresis, and transferring into distinct containers the liquid from the distinct regions. The liquid may be transferred through capillary tubes or by contacting the structure containing the through-holes with the surface of the liquid.

In accordance with other embodiments of the invention, a method is provided for manufacturing a platen having two substantially parallel planar surfaces and a plurality of through-holes disposed substantially perpendicularly to the planar surfaces. The method has the steps of providing a sheet of thermoplastic material, loading the sheet of thermoplastic material into contact with a surface of a die having a plurality of holes, and bringing a punch having a plurality of protrusions of specified cross-section into contact with the sheet of thermoplastic material in such a manner that the protrusions are in alignment with the holes of the die such that through-holes are cut through the thermoplastic material. In an alternate embodiment of the invention, a sheet of electrically conducting material is loaded into contact with a surface of a die having a plurality of holes and an EDM mandrel having a plurality of protrusions of specified cross-section is brought into proximity of the sheet of conducting material in such a manner that the protrusions are in alignment with the holes of the die, and through-holes are cut through the conducting material.

Another embodiment of the invention provides a method for applying a hydrophobic coating to a silicon platen having a first and a second surface, the surfaces being substantially parallel, and a plurality of through-holes substantially perpendicular to the surfaces. The method has the steps of oxidizing the first surface, cleaning the oxidized first surface, applying a positive pressure of inert gas to the plurality of through-holes from the direction of the second surface, and exposing the first surface to a silanizing vapor agent.

In accordance with other alternate embodiments of the invention, a method is provided for loading a liquid into a plurality of through-hole platens having the steps of stacking at least two platens together in such an adjacent manner that at least one of the plurality of through-holes from each platen is registered with a through-hole of each other adjacent platen so as to form at least one continuous channel, and transfering the liquid into each continuous channel. Each platen may be separated from each adjacent platen by an air gap, and the liquid may be transferred with capillary tubes or at least one cannula.

A method for mixing liquid that is contained in through-holes of at least two platens is provided that includes stacking the platens together for a specified time, in such a manner that at least one of the plurality of through-holes from each platen connects with a corresponding through-hole of another platen and liquid is allowed to diffuse between connecting through-holes. The platens may then be separated after the mixing.

In accordance with yet further alternate embodiments of the invention, a method for humidifying a system is provided, where the method has the steps of filling a microchannel plate with a liquid having a plurality of parallel microchannels and placing the filled microchannel plate in vicinity of the system to be humidified.

Another alternate embodiment of the invention provides a method for diffusing light. According to this method, a fluid is entrained in substantially each of a plurality of parallel microchannels having proximal and distal ends, the microchannels comprising a microchannel plate. The proximal end of each of the plurality of parallel microchannels is illuminated with light and diffuse light emanates from the distal ends of the microchannel.

In accordance with yet another embodiment of the invention, a perforated platen is provided for manipulating distinct liquid samples of volume less than 1 microliter. The platen has an inner layer of hydrophilic material and two outer layers of hydrophobic material coupled to opposite sides of the inner layer, and a two-dimensional array of through-holes, at least two holes having distinct volumes, for retaining the distinct liquid samples, the through-holes each having a diameter less than 300 micrometers and traversing the inner layer and the two outer layers in a direction substantially perpendicular to each of two planar surfaces of the platen.

BRIEF DESCRIPTION OF THE DRAWINGS

The invention will be more readily understood by reference to the following description, taken with the accompanying drawings, in which:

FIG. 2a is top view of a portion of the platen of FIG. 1a in which the through-holes are configured on rectangular centers;

FIG. 2b is top view of a portion of the platen of FIG. 1a in which the through-holes are configured in a hexagonal close-packed array;

FIG. 22b is a cross-sectional side view of the a portable humidity chamber of FIG. 22a.

DETAILED DESCRIPTION OF SPECIFIC EMBODIMENTS

The Through-Hole Array

In accordance with the present invention, methods are provided for producing different chemical reactions within an array of through-holes. The invention is advantageously employed, for example, in screening operations, where different reaction conditions are advantageously provided among the various through-holes of the array. As an example of the many modalities of use of the invention, different chemical species may be loaded into different through-holes of the array, and concentrations of the various species might also be differentiated among the various through-holes. The invention may thus provide a method for screening compound libraries, for example, to predict the ability of each compound to be absorbed by a patient.

Figure 1A:
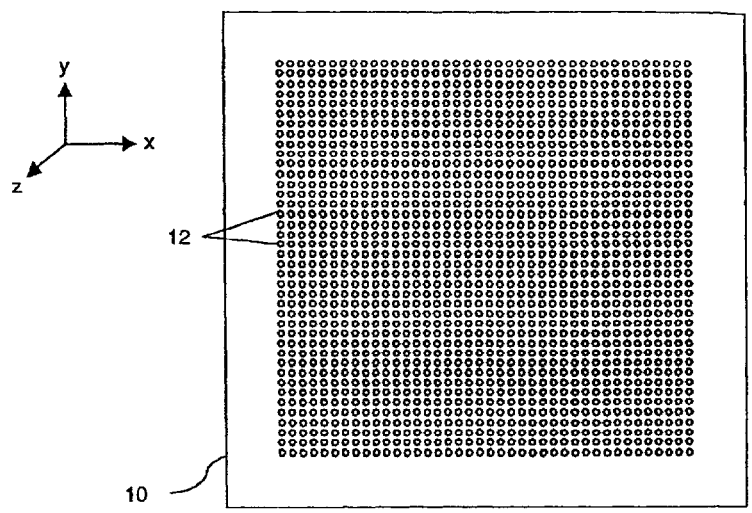
FIGS. 1a and 1b show a top and exploded cross-sectional views, respectively, of a high-density array of through-holes in accordance with one embodiment of the present invention.
Figure 1B:
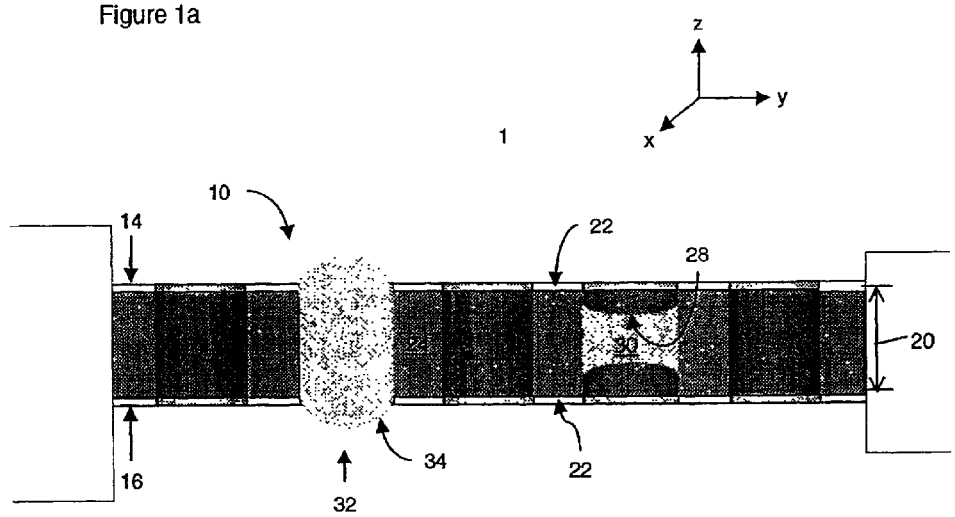

In accordance with preferred embodiments of the invention, a high-density array of through-holes is provided, as now discussed with reference to FIGS. 1a and 1b. FIG. 1a shows a top view of a platen 10, otherwise referred to herein as a "substrate," "sample wafer," or "through-hole plate." Platen 10 is the carrier of a large number of through-holes 12 which traverse platen 10 from a top surface 14 to an opposing surface 16 of the platen, as shown in the cross-sectional side view of FIG. 1b. While the term "platen" may refer to a structure having substantially parallel plane surfaces and transverse dimensions substantially exceeding the thickness of the structure, alternative geometries are within the scope of the present invention, and use of the term "platen" is not restrictive. A prism-shaped geometry is described below, for example.

Through-holes 12 constitute assay wells (or "microwells") in accordance with an embodiment of the invention. Through-holes 12 may be shaped as circular right cylinders, or, alternatively, may have rectangular cross-sections. Otherwise-shaped through-holes are also within the scope of the present invention.

While through-hole plate 10 is preferably made of conductive silicon, other types of rigid materials, such as metal, glass, or plastic may be used provided that the material is chemically inert with respect to the sample substances, or can be rendered so by appropriate surface treatments.

Each through-hole 12 is typically of a substantially square cross-section, although geometries, such as circular or rectangular cross-sections may be used. Through-holes 12 are also referred to herein as "channels."

Figure 3:
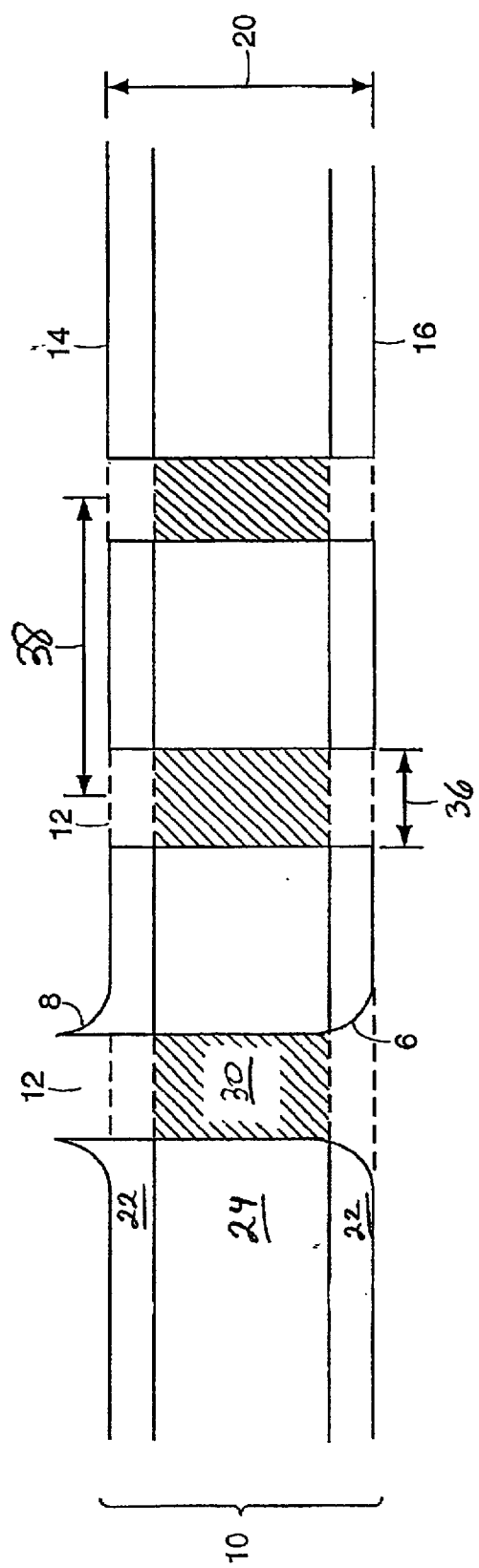
FIG. 3 is a further side view in cross-section of a portion of a laminated platen containing multiple through-holes for analysis of liquid samples in accordance with a preferred embodiment of the present invention.
Figure 4:
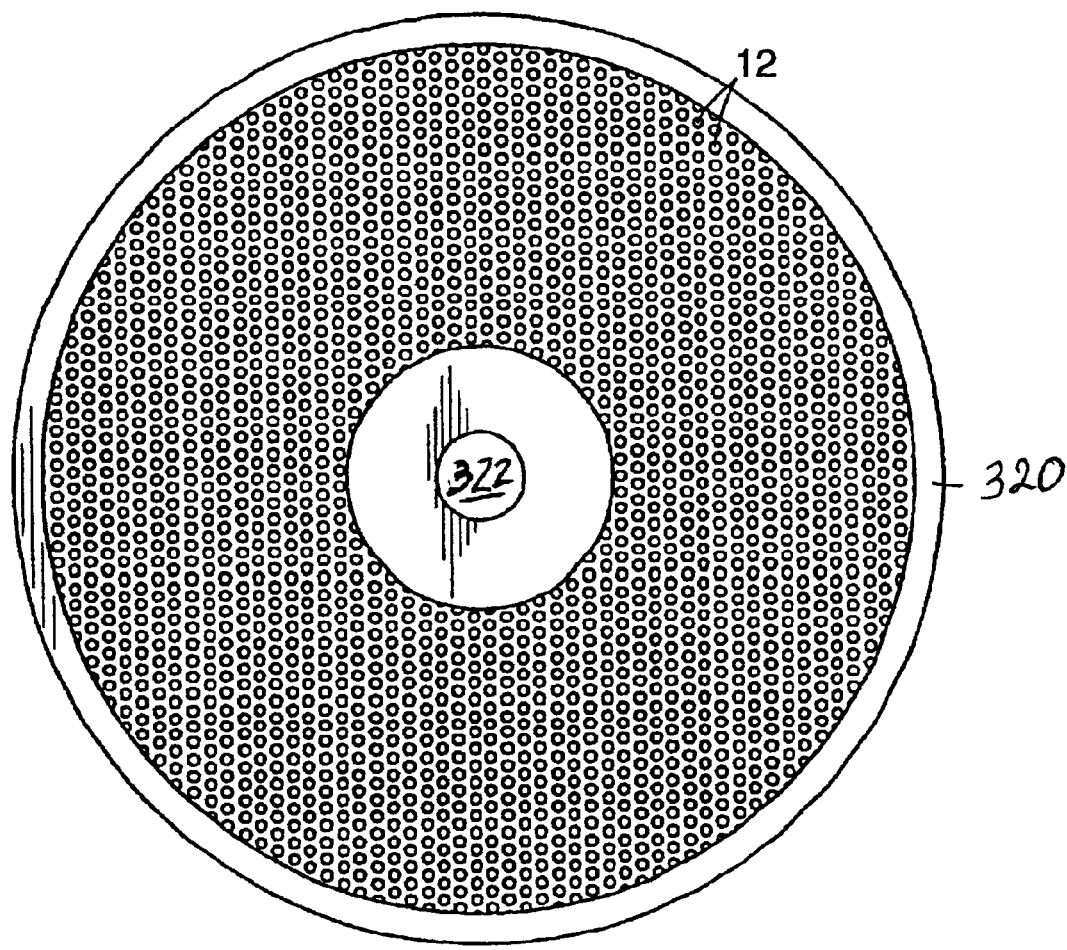
FIG. 4 is a top view of round sample wafer populated with through-holes in accordance with an embodiment of the present invention.

Through-holes 12 may be centered on a rectangular grid, as shown in FIG. 2a, or in a close-packed hexagonal lattice, as shown in FIG. 2b. Referring to FIG. 3, a typical thickness 20 of platen 10 is on the order of 0.5–2 mm, while through-holes 12 have typical characteristic dimensions (such as diameters) 36 of on the order of 100–400 $\mu$m. Thus the volume of each through-hole 12 between surface 14 and surface 16 is on the order of $\sim 10^{-7}$ cm$^3$ or greater. Through-holes 12 are spaced on centers typically on the order of twice the diameter of the holes, although all spacing configurations are within the scope of the invention and of the appended claims. In particular, a hole-to-hole spacing 38 of 500 $\mu$m is typically employed, which corresponds to an array density of 400 holes per square centimeter of plate. In accordance with manufacturing methods described below, microwells are produced for the assay of a chemical or biochemical reaction where the volume of each microwell may be less than 100 nanoliters ($10^{-7}$ cm$^3$). The packing density of wells may thereby be increased by several orders of magnitude over prior art technology.

Grouping of through-holes into smaller sub-arrays may also be used, and, more particularly, a reproducible pattern may be applied to a plurality of the sub-arrays. Each through-hole 12 may be identified by its own address within the array.

Referring, again, to FIG. 1b, platen 10 may also advantageously be formed of a laminate of materials, with a central layer 24 and outer "sandwiching" layers 22. In order to enhance capillary loading of sample 30 into the microwell and to prevent capillary outmigration of the sample liquid, exterior sections 22 of the microwell, adjacent to surfaces 14 and 16 of platen 10, have a hydrophobic wall surface in accordance with a preferred embodiment of the invention, while the interior section 24 of the through-hole wall has a hydrophilic surface thereby preferentially attracting an aqueous liquid sample. In a similar manner, an array having hydrophilic faces and hydrophobic through-holes may be uniformly filled with a low surface tension liquid such as an alkane. The hydrophobic layers on either end of the well are on the order of 1 $\mu$m thick or less. On loading the sample liquid into the microwells, each well is typically overfilled by about 10% above the volume surrounded by the four walls of the microwell. Under these circumstances, liquid sample 30 may form convex meniscus surfaces 34 on both the upper and lower surfaces of the sample.

An underfilled microwell 26 will typically be characterized by a liquid sample exhibiting a concave meniscus 28 on both the upper and lower surfaces of liquid sample 30.

The apertures of through-holes 12 need not be square, and, in accordance with an alternate embodiment of the present invention, flanges 8 may extend above planar surface 14 surrounding some or all of through-holes 12 while indentations 6 may be fabricated rounding the edges of through-holes 12 at opposing surface 16. Flanges 8 and indentations 6 may advantageously provide for registration of successive platens 10, in the case where platens are stacked, and in processes of mixing or dilution, as discussed in detail below.

Through-holes 12 may be loaded with a first sample 18 in liquid form. Sample 18 is allowed to react with a second sample where the second sample may include a variety of test samples and by subsequent or concurrent analysis of the reaction products, using, for example, optical markers, a large number of reactions may be processed and analyzed in parallel.

As applied to biological assays, by way of example, first sample 18 may be a solution containing pharmacologically relevant proteins or other molecules. Such a solution may include, for example, cells in aqueous suspension, eukaryotic (animal, yeast) or prokaryotic (bacteria) cells, hybrid cells, and biological molecules including, for example, antibodies and enzymes, although application to other biological or non-biological assays is within the scope of the invention as claimed herein. All such reagents may also be referred to herein and in the appended claims as "targets." Typical yeast cell concentrations of $10^7$ cells per milliliter of solution yield on the order of 1000 cells per 100 nanoliter well. Typically, an entire chip or the subset of through-hole wells constituting a contiguous region of platen 10 may be populated with a single strain of cells.

A typical procedure assay procedure, such as may be employed in pharmaceutical research, entails the subsequent addressed introduction of a test sample including one or more analytes into the through-hole wells, with selected materials introduced into subsets of through-holes that may include one or more through-holes. The test sample addressably introduced into the subsets of through-holes may contain drug candidates or known drugs. The test sample may be comprised of multiple components, introduced at the same time or sequentially. Components of the test sample may include analytes, antagonists, reagents, solvents, or any other materials and may be introduced in liquid form or otherwise. In accordance with a preferred embodiment of the invention, test samples are introduced into the through-hole wells in liquid form in order to facilitate rapid reaction via diffusion with first sample 18 already resident in liquid form in the through-holes.

The set of substances from which the second sample addressed to a particular through-hole site is drawn is referred to in this description and in the appended claims as a "library" of substances. In typical applications, the library is of a substantial size and thus advantageously utilizes the capability of the present invention to facilitate parallel reaction and analysis of large numbers of substances. In pharmaceutical applications in particular, libraries may be composed of between $10^3$ and $10^9$ substances and combinations of substances.

Figure 1C:
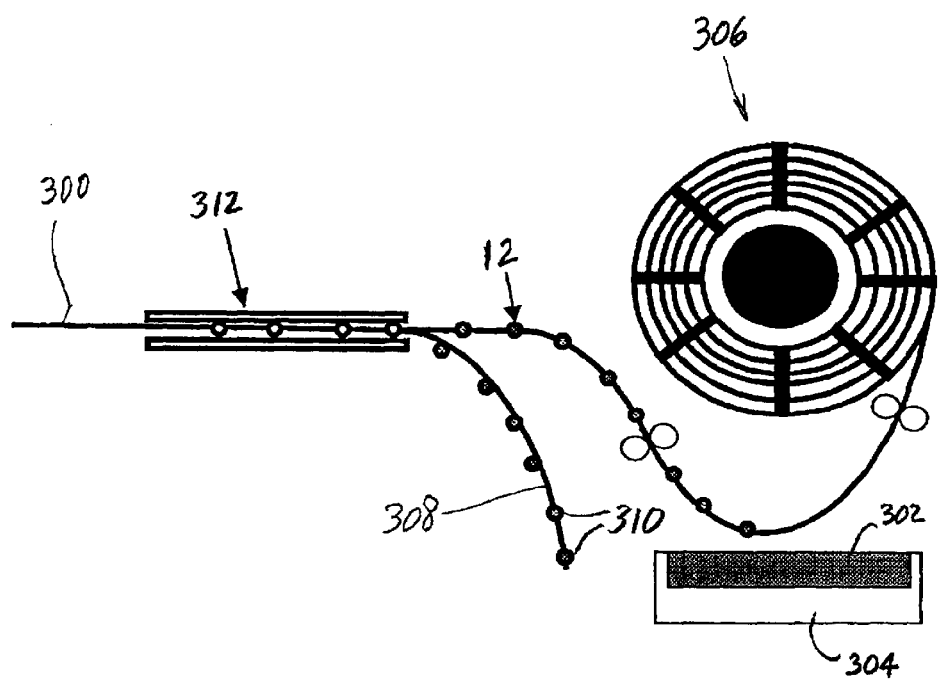
FIG. 1c shows a schematic side view of a continuous sheet array of through-holes in accordance with another embodiment of the present invention.

Referring now to FIG. 1c, the throughput of a screening system incorporating arrays of through-hole sample containers may be further increased by using a continuous sheet 300 of through-holes 12. The interiors of the through-holes may be hydrophilic, as described above in reference to FIG. 1b, and the surface of sheet 300 may be hydrophobic, as also described. Through-holes 12 may be filled in a continuous manner by passing sheet 300 through an aqueous medium 302 contained in fluid trough 304. After through-holes 12 have been filled, sheet 300 may be wound onto a spool 306 or cassette for storage followed by assay, or, alternatively, may be assayed directly. Assays may be by optical readout such as fluorescence absorbance or chemi-luminescence measurements, all of which may be performed by passing the sheet across an optical detector such as a CCD array.

Sample array sheets 300 are preferably produced with registered holes, either by precision production processes or in matched sets. The sheet composition may be a polymer, elastomer, or metal, including an amorphous metal. Multiple sheets may be mated in the same way that platens of through-holes may be stacked, as described below, for example, with reference to FIGS. 16–19, in order to initiate reactions, or for other purposes. FIG. 1c shows a second sheet 308 of through-holes 310 being brought into contact with sheet 300 in mixing area 312 for mixing of the liquid contents of the respective through-holes. Examples of applications involving this embodiment include, screening genetic libraries or screening combinatorial chemical libraries contained on polymer beads. These embodiments of the invention may advantageously include extremely high throughput, reduction or elimination of high-cost automation components, and the small size of a screening system with sample handling and detection modules. The holes in the sheet may be, if desired, produced online with an array of punches or UV lasers.

As an example of an application in which a genetic library is screened for improved enzymes using a one step assay, an *E. coli* genetic library is prepared containing mutations in the beta galactosidase enzyme. The *E. coli* cells are grown to a density in phosphate-limited media such that there is an average of 1 cell for every 200 nl of liquid. The media also contains, MUG, a fluorogenic substrate for beta-galactosidase. A through-hole sheet is prepared with a hydrophobic exterior and hydrophilic through-holes at a density of 10^7 per square meter. Registration holes are includes in the tape to aid in precise dispensing. Each through-hole holds 70 nl of fluid. A spool of the through-hole sheet is unwound and guided through a trough containing the cell solution, so that each through hole is filled. The sheet is then wound onto spacers and into a receiving spool. The spacers prevent smearing of the liquid and provide for gas transfer in and out of the spool. The spool is incubated in a humidified enviroment at 37° C. for 24 hours. The spool is then unwound as it is passed between a uniform photo-illumination source with a wavelength of 350 nm and a CCD imaging system with a 450 nm filter. The position in the sheet of colonies with exceptionally high enzyme activity is recorded and those colonies are retrieved using a robotic microfluid handling system for further analysis. This assay can also be performed by co-registering and mating a second, identical, sheet containing the fluorogenic substrate with the first sheet containing the bacteria. An absorbance measurement may also be performed to normalize the signal output for the number of bacteria.

In accordance with another alternate embodiment of the present invention, described with reference to FIG. 3, through-holes 12 may be disposed in an array within a circular sample wafer 320 having a central hole 322 for purposes of centering with respect to handling equipment.

Referring now to FIG. 5, platen 10 and through-holes 12 may assume other geometries than have heretofore been described, in accordance with alternate embodiments of the invention. The volumes of the through-holes may be varied as a known function of spatial location in the array. The volume of a through-hole $V=k\ s^2 l$, is a function of lateral hole dimension, s, length, l and constant k that depends on the specific cross-sectional hole geometry. The cross section may be varied, as depicted in FIG. 5a, as a known function of spatial location within the array by changing the hole's lateral dimensions as a function of position within the array. The hole volume scales as $s^2$; thus increasing the hole dimensions by a factor of 3.3 increases the volume by a factor of 10. One example is in a plane parallel plate, the hole dimensions are increased as a linear function in one or both lateral directions.

Figure 5A:
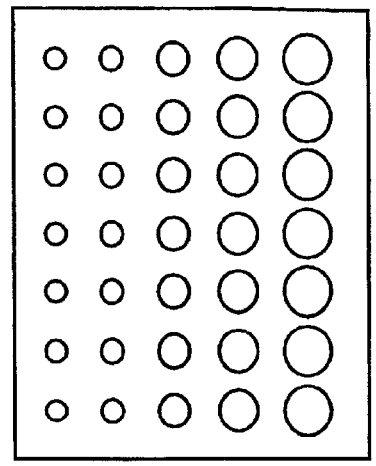
FIGS. 5a–5d show examples of arrays with through-hole volumes that are a function of array position.
Figure 5C:
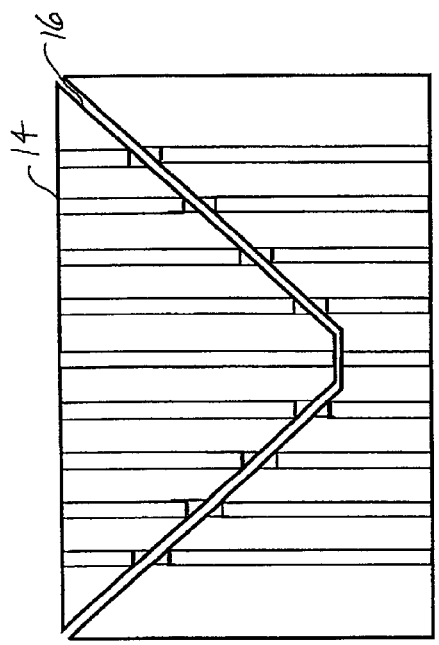
Figure 5B:
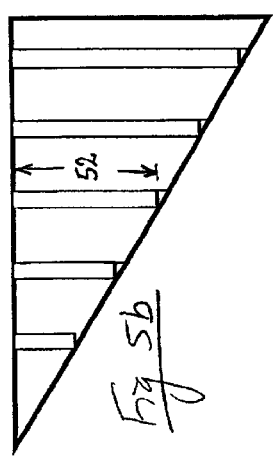
Figure 5D:
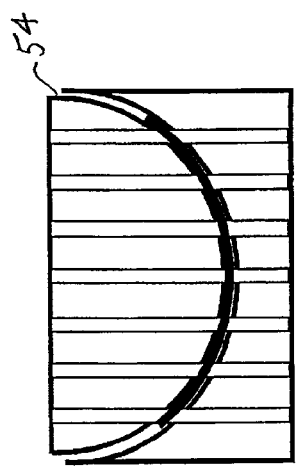
Figure 5E:
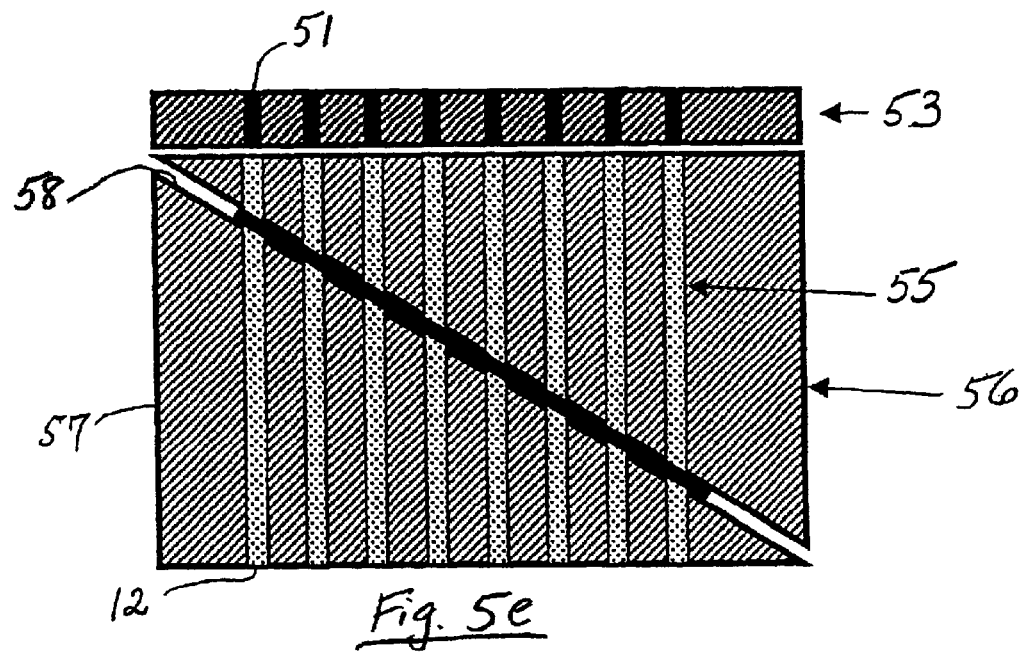
FIGS. 5e and 5f show cross sections of through-hole prisms as employed for massively parallel liquid chromatography or electrophoresis, in accordance with embodiments of the present invention.

Another method to produce different through-hole volumes as a function of array position is to change the distance between top and bottom surfaces of the plate defining the hole length 52, as shown in FIG. 5b. One particular example is to incline the plate top 14 and bottom 16 surfaces at an angle to each other as in a wedge or prism, as shown in FIG. 5c. In this example, the volume change is linear with distance along the array in the direction of surface inclination while in the orthogonal direction along a row of holes, the hole length, and thus volume, is constant. In accordance with another alternate embodiment of the invention, an array can be fabricated from a contiguous series of planar surfaces inclined to each other in either one- or two-dimensions such that the through-hole volume is different in both directions along the array. In yet a further embodiment, an array is fabricated from a non-planar surface 54 such as a surface of hemispherical curvature as shown in FIG. 5d.

Figure 6:
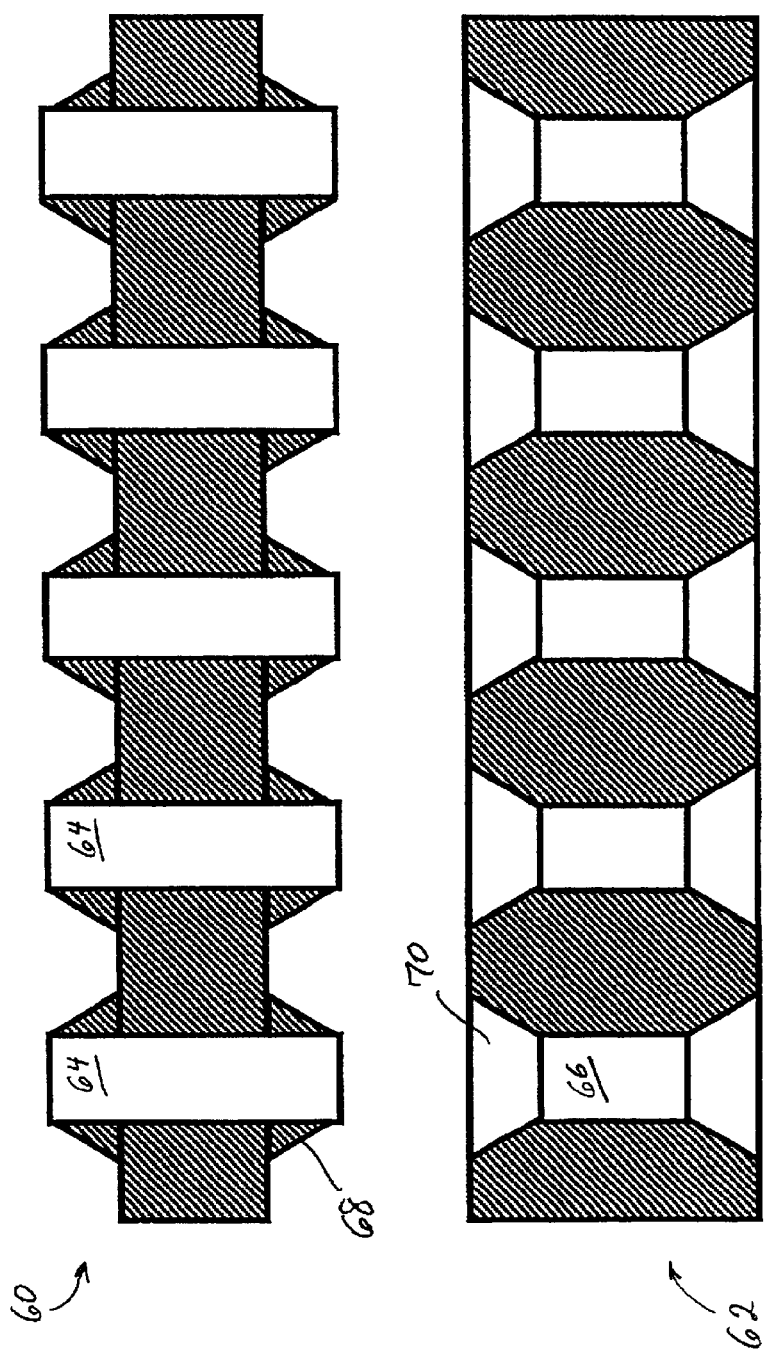
FIG. 6 shows an example of an interlocking array.

For each array geometry, a second array fabricated having surfaces that are the complement of the first array's geometry may be used, in accordance with alternate embodiments of the invention, to facilitates vertical stacking of the arrays, as shown in FIG. 6. Alignment of through-holes 64 of plate 60 with through-holes 66 of plate 62 is provided by inserting protruding segments 68 into corresponding indentations 70. Other array geometries with greater than four-fold rotation symmetry with respect to the array surface normal will facilitate interlocked and self-aligned stacking of arrays with matching positive and negative geometries, within the scope of the present invention. This geometrical arrangement may advantageously obviate the need for alignment pins which are typically required for registration of stacked planar arrays.

Applications of Arrays of Non-Uniform Volume

One application of arrays having through-holes of non-uniform volume is mixing of different volumes of liquids such as in a dilution sequence, as described below. An advantage of this method is that stacking of multiple arrays, as also described below, may be obviated while a wide range of dilution may be achieved.

Another application of arrays of either constant or non-uniform through-hole volumes is fraction collection from chromatographic elution. The through-hole array advantageously provides the ability to collect a large number of small volume fractions, which can then be further separated within the through-hole array, as described below. This, in turn, advantageously increases the resolution of chromatographic separation over prior technology.

Figure 5F:
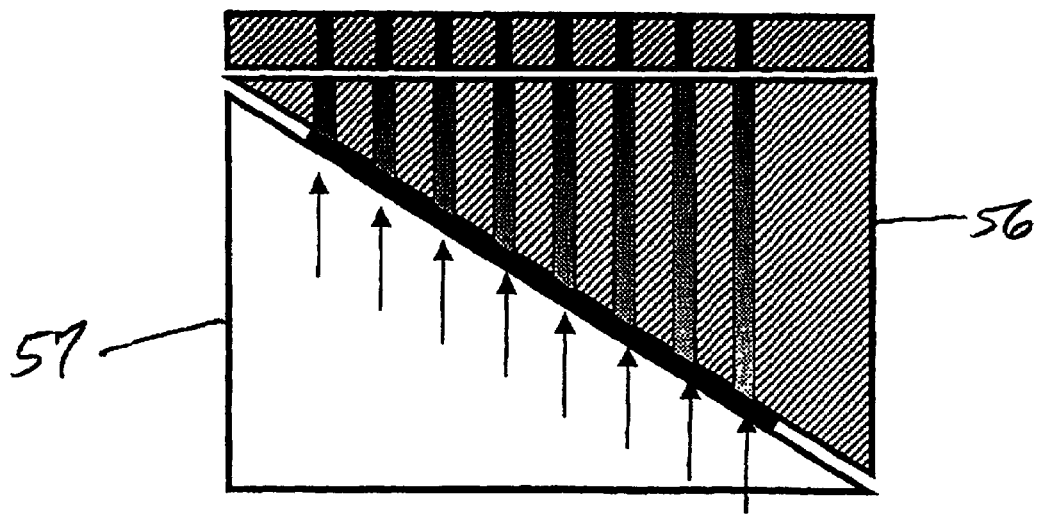

Yet another application of non-standard array geometries is for massively parallel liquid chromatography or electrophoresis. More particularly, referring to FIG. 5e, a through-hole plate 56 is employed whose thickness increases in one lateral direction (such that the plate has the shape of a prism) resulting in a linear increase in hole length with array position. A second through-hole prism 57 is brought together with the first prism 56 along their common hypotenuse 58 thereby producing an array of through-holes 12 of substantially equal length. To use this structure as a liquid chromatography column, each hole is filled with a porous gel 55 characteristic of liquid chromatography. The sample 51 to be analyzed is applied to one end of the array, as from a sample plate 53, for example, and a pressure is applied to drive fluid sample 51 through each hole. Each component in the mixture will travel at a different velocity through the gel matrix resulting in a separation of the mixture along the column length. For example, small molecules will move rapidly through the channel to its opposite end, whereas, after the same duration of time, larger molecules may typically have traveled only a fraction of that distance. The intersection of each through-hole with the hypotenuse along which the prisms are joined corresponds to different travel lengths along the chromatographic column. Separation of the array into its constituent prisms, as depicted in FIG. 5f, gives a "snapshot" of the mixture components distributed as a function of array position. Rather than a function of time, the chromatograph is transformed into a function of position by running identical samples in an array of columns with a known inter-column delay, expressed either as a time, or, equivalently, as a length. By sequentially analyzing the material output from each through-hole along the direction of increasing plate thickness, an equivalent chromatograph can be reconstructed. Further mixture separation is possible if the gel porosity is made different in the array direction orthogonal to the wedge orientation. Decreasing gel porosity further increases the retention time for each component, thus leading to finer resolution of the mixture components. Electrophoretic separation may be achieved in an analogous manner, where an applied electric field is the driving force.

Fabrication of the Through-Hole Array

Figure 7:
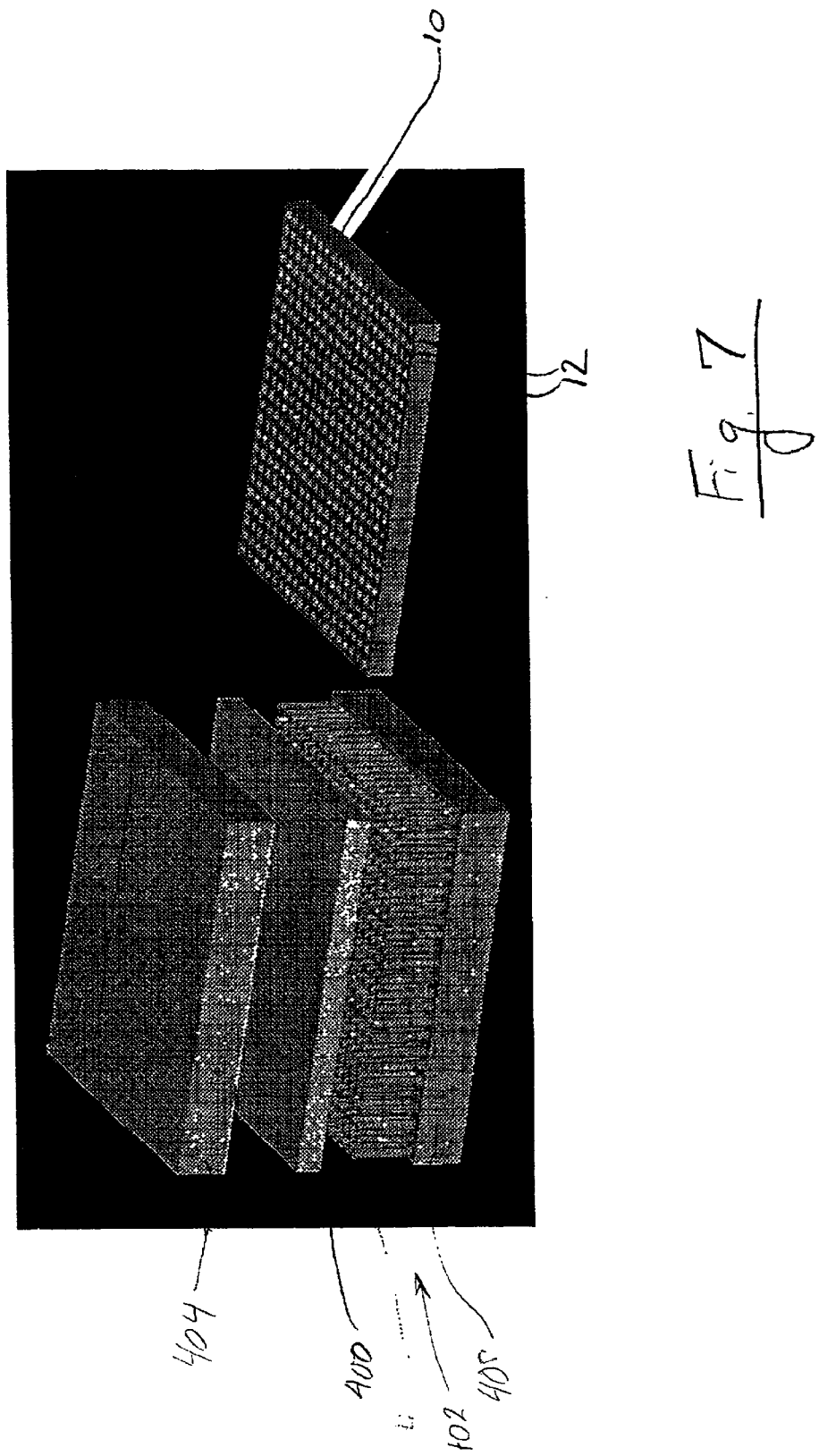
FIG. 7 depicts the configuration of a compression mold for compression molding on an array of through-holes in accordance with an embodiment of the present invention.

Referring now to FIG. 7, through-holes 12 may be formed in platen 10 by any of a variety of means appropriate to the material of platen 10. Through-hole forming methods include, by way of example, laser ablation by means of an ultraviolet (UV) excimer laser which may form 100 $\mu$m through-holes in glasses and polymers. Additional through-hole forming techniques include mechanical drilling, electrochemical methods such as micro-electrical spark discharge machining (EDM), employing radio-frequency pulses for ionizing removal of conductive materials, or, in accordance with other embodiments of the invention, by selective chemical or charged-particle etching techniques. Additionally, microcapillary bundles of glass fibers of varying compositions may be drawn from preform and sliced to form platens, and then selectively etched to form through-holes.

As shown in FIG. 7, through-holes 12 may be formed, in materials such as thermoplastics or polycarbide, by punching platen blank 400 using punch array 402 and die array 404, in conjunction with a high-pressure ram. Punching pins 406 may be formed in punch block 408 using microwire EDM, as described in detain in the following discussion, or by microetching techniques such as chemical or charged-particle etching. Additionally, punch array 402 may be formed using microsawing techniques. Die array 404 is similarly formed using microfabrication techniques known in the manufacturing arts.

High-density arrays of through-holes may be formed in conducting materials, including conductive (>10 $\Omega^{-1}$-cm$^{-1}$) silicon wafers, using a combination of wire and die sink EDM. EDM is typically used in the preparation of tooling dies for injection molding. As is well known, the machining process involves ionizing away the surface of a conducting material, typically a metal. EDM can be performed using a tip-based electrode, or a "wire." Wire-EDM is used when fine surface finishes are required, or when subtle machining features not achievable with a tip electrode are desired. Traditional wire-EDM machining utilizes wire approximately 250 $\mu$m in diameter. Due to the small dimensions and high packing densities of the invention an adapted microwire EMD process is used that employs wires with diameters down to 30 $\mu$m. This system may provide surface finishes down to 100 nm, essentially a mirror finish.

Figure 8:
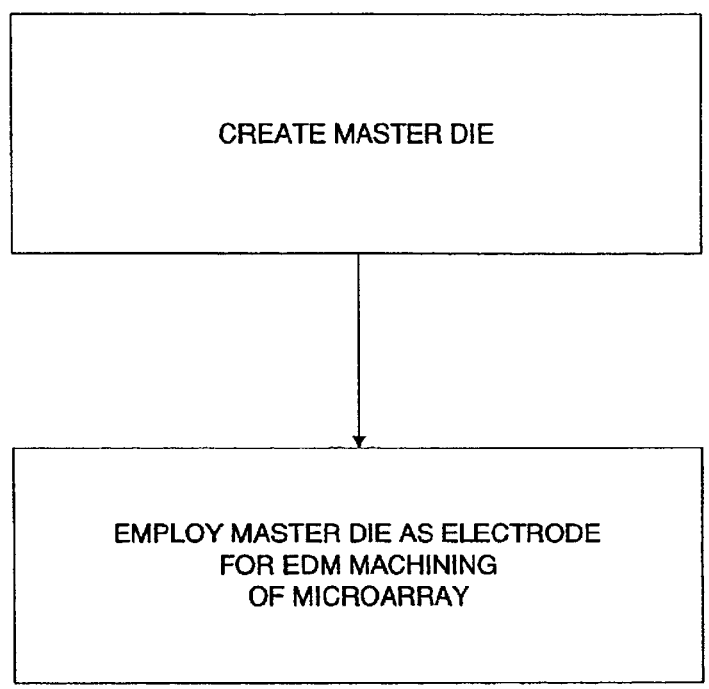
FIG. 8 is a flow chart depicting steps in the fabrication of a through-hole array by EDM, in accordance with an embodiment of the invention.

Referring to FIG. 8, a typical method for preparing a through-hole array using microEDM machining follows a two-step process. The first step is the creation of a positive or master die. The second step uses another EDM machine called a "sink-EDM." The sink-EDM machine uses the master as an electrode and thereby creates a negative copy in the machined conducting material. This negative copy is the resulting microarray. The master electrode can produce multiple negatives before needing to be replaced, thereby increasing manufacturing throughput for production of the chips.

In contrast with deep reactive ion etching—the process commonly used to produce high aspect ratio structures in silicon—the EDM technique described herein may advantageously reduce fabrication time and cost.

After the master die is fabricated with wire EDM, it may typically be used to sink an array of microchannels through a 0.5-mm thick silicon wafer in less than two minutes. Additional machining time, during which the master die moves largely in the plane of the array, is typically needed to enlarge the holes to the desired dimension and to improve the surface finish. The fabrication process described has been used to sink microchannels of sizes up to 10,000 elements with cross-sections <300 $\mu$m×300 $\mu$m and element spacings <500 $\mu$m. Another advantage of this technique is that it may also be used to a manufacture stainless steel precision alignment jig that is used to align the chips for mixing and optical readout, as described herein.

Combined with the precision alignment jig, this EDM process results in <10 $\mu$m center-to-center total error in channel spacing across the entire array. This guarantees accurate hole alignment across arrays, and when combined with the hydrophobic exterior coating, minimizes cross talk between microchannels.

Referring again to FIG. 7, the master die 408 produced from the process outlined above can be used to create the through-hole arrays from a plastic blank 400. In this approach the die is used as a type of punch to create the through-hole array from a solid piece of plastic. Unlike a punch, however, the master does not force its way through the plastic. Instead, by having the appropriate kinetic energy as it impacts the plastic it essentially vaporizes the solid plastic into low molecular weight gases (with some residual energy dissipated as heat). In this manner the master can be removed from the resulting through-holes without having melted into it. A slight taper on the protrusions of the master that forms the channels facilitates removal of the master from the chip. This process is similar to that which is used in the manufacturing of DVD's, except the manufacture of microwell arrays typically requires significantly greater penetration depths (up to 1 mm deep). Alternatively, plastic microwell plates may be manufactured by injection molding of metal masters formed by EDM.

As discussed above, with reference to FIG. 1b, it is desirable to prevent cross-communication between the various through-holes during loading and other operations by coating the surfaces of the platen with a hydrophobic coating 22. It is also desirable to coat the inner surfaces of the through-holes with a hydrophilic coating 24 so that they retain fluids. In accordance with embodiment s of the invention, the inner coating 24 may be chemically blocked to prevent non-specific binding or derivatized with affinity ligands.

In accordance with preferred embodiments of the invention, a dense array 10 of through-holes 12 is produced in silicon and coated in silicon oxide by oxidation. The surfaces of the conductive silicon are covered in a thin oxide layer. The wafer is then cleaned by soaking in a mixture of hydrogen peroxide and sulfuric acid, or other caustic solvent cleaning solution, to remove organic materials. Clean silicon oxide thus produced has a high surface energy. The top and bottom faces of the arrays are made hydrophobic by exposing them to vapor from a solution containing an appropriate silanizing agent (such as polydimethylsiloxane, sold as Glassclad 216™ by United Chemical Technologies, Inc.) in a volatile solvent. The silanizing agent reacts with the hydroxyl and silanol groups on the array surface and creates covalent bonds to hydrophobic alkyl groups.

The resulting coated arrays can be uniformly loaded with aqueous solutions by simply dipping the array into it. The liquid instantaneously fills the channels through capillary pressure, but does not wet the other surfaces. Hydrophobic coatings produced in this way are stable under high humidity and they can be used repeatedly over several days. Other surface chemistries may be exploited to attach hydrophobic chemical groups to the faces of arrays made from other materials. For example a gold-coated surface reacts with alkane thiols to attach a hydrophobic alkyl groups, as discussed by C. D. Bain et al., *J. Am. Chem. Soc.*, vol. 111, pp. 321–325 (1989), which reference is incorporated herein by reference.

In accordance with other embodiments of the present invention, the surface chemistry of the array faces may also be selectively modified by substituting other silanizing agents for the polydimethylsiloxane telomer. This method may advantageously prevent aqueous solutions from adhering to array faces during array loading and also act as physical barriers between the aqueous solutions in adjacent through-holes. During this process a positive pressure of inert gas is applied to the opposite side of the array. The positive pressure within the through-holes prevents the silanizing vapor from reaching the interior surfaces. This method advantageously allows removal and reapplication of the hydrophobic coating.

Array Loading Techniques
Dip Loading

Figure 9C:
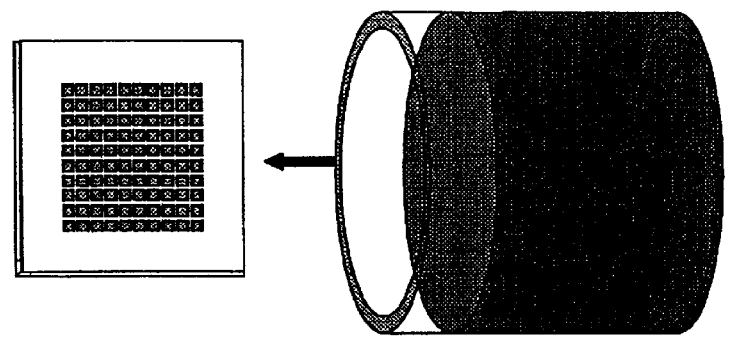
FIGS. 9a–9c depict a sequence of operations for filling a through-hole array with a first liquid.
Figure 9B:
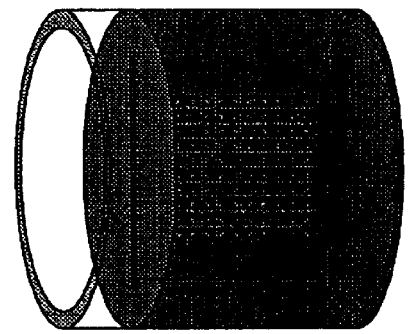
Figure 9A:
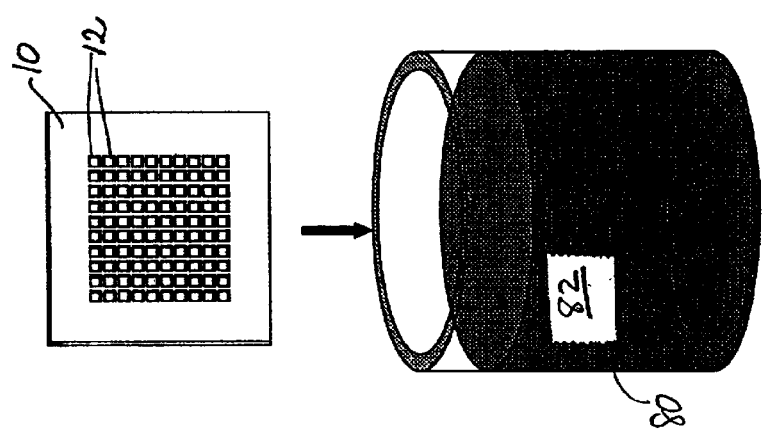

Referring now to FIGS. 9a–9c, array 10 of through-holes 12 may be filled using techniques either that directly address particular through-holes, or techniques that fill the entirety of the array according to a specified pattern based on composition, concentration of a substance, etc. Dip loading may be employed, for example, in order to fill an entire array with the same solution. A through-hole array 10 is produced and chemically treated to make the array faces hydrophobic and the through-hole surfaces hydrophilic. Plate 10 with through-holes 12 is first lowered into a container 90 containing a first liquid 82, as shown in FIG. 9a. Once plate 10 is fully immersed in the first liquid, it is shaken so that first liquid 82 displaces the air in each of the through-holes, and all the through-holes 12 are filled with first liquid 82. All means of replacing the air in the through-holes is within the scope of the present invention, whether by shaking, applying a vacuum to one side of plate 10, employing electrostatic forces, tilting the plate so that the air is displaced by virtue of its buoyancy, all cited as examples and without limitation, or else by other means. After through-holes 12 have been filled, plate 10 is withdrawn from first liquid 82, as shown in FIG. 9c. The array is typically withdrawn slowly such that the surface of the fluid in the reservoir pulls excess liquid off of the non-wetting array surface. Alternatively the array may be filled with water by spraying the array with water or by sonicating the array in a reservoir of water in order to remove trapped air bubble prior to dip loading. In this case, less agitation is required to uniformly fill the array with solution.

Both convection and diffusion can be used to induce mixing between fluids in microchannel arrays. This can be demonstrated by filling a microarray with aqueous solution of blue dye and by submerging the microarray into a beaker of still water to induce dilution via diffusion. A small mechanical disturbance (such as a tap to the side of the beaker) causes rapid replacement of the blue dye by water. Alternative methods for filling the array with water include spraying the array with water or sonicating the array in a reservoir of water in order to remove trapped air bubble prior to dip loading are also within the scope of the present invention.

Similarly, an array having hydrophilic faces and hydrophobic through-holes may be uniformly filled with a low surface tension liquid such as an alkane.

Loading by Dragging Droplet Along Array Surface

Droplet dragging is performed to load an entire array or a group of channels within a single array with the same fluid. It is appropriate for loading samples which must be conserved because of cost or availability. To perform a loading operation by dragging, a droplet of the loading solution is formed on the end of a syringe needle, micropipette or other fluid dispensing capillary. The drop is placed on the array face over the through-holes to be filled. The capillary is then moved to drag the drop across the surface of the array and over the channels to be filled. Surface tension maintains contact between the capillary tip and the fluid drop. When the drop is depleted additional fluid is dispensed until all desired through-holes have been filled. The capillary and any remaining fluid in the drop are then withdrawn from the array surface.

Transfer of Liquids between Microtiter Plates to Through-hole Array

In accordance with further embodiments of the invention, a method is provided to transfer liquids from standard microtiter plate formats (96-, 384-, or 1536-wells, for example) to a single array of through-holes or multiple, vertically stacked arrays in which holes in the same spatial location from one array to the next are co-registered. As used herein, the term "registration" refers to aligning a through-hole plate with at least one other through-hole plate, such that the tops of a plurality of through-holes of one of the plates coincide with the bottoms of a plurality of corresponding through-holes of the other plate or plates, thereby creating a plurality of contiguous channels.

All of the filling examples given can be performed in parallel on a single array stack with multiple capillary tubing arrays filled with liquids from different microtiter plates or the same microtiter plate. Fluid may be transferred from chemical libraries stored in 96- and 384-well microfiter plates quite rapidly with these methods. For example, if 100 arrays with $10^5$ through-holes per array are to be filled with liquid stored in 96 well plates, and if each transfer operation (plate exchange, fluid loading and transfer) takes approximately 20s, then the requisite arrays may be filled within approximately six hours. The filling operations take place preferably in an environmentally-controlled chamber (temperature, humidity, atmosphere, etc.), as described below.

Transfer of Liquids from Microtiter Plates to One or more Through-hole Array

Figure 10:
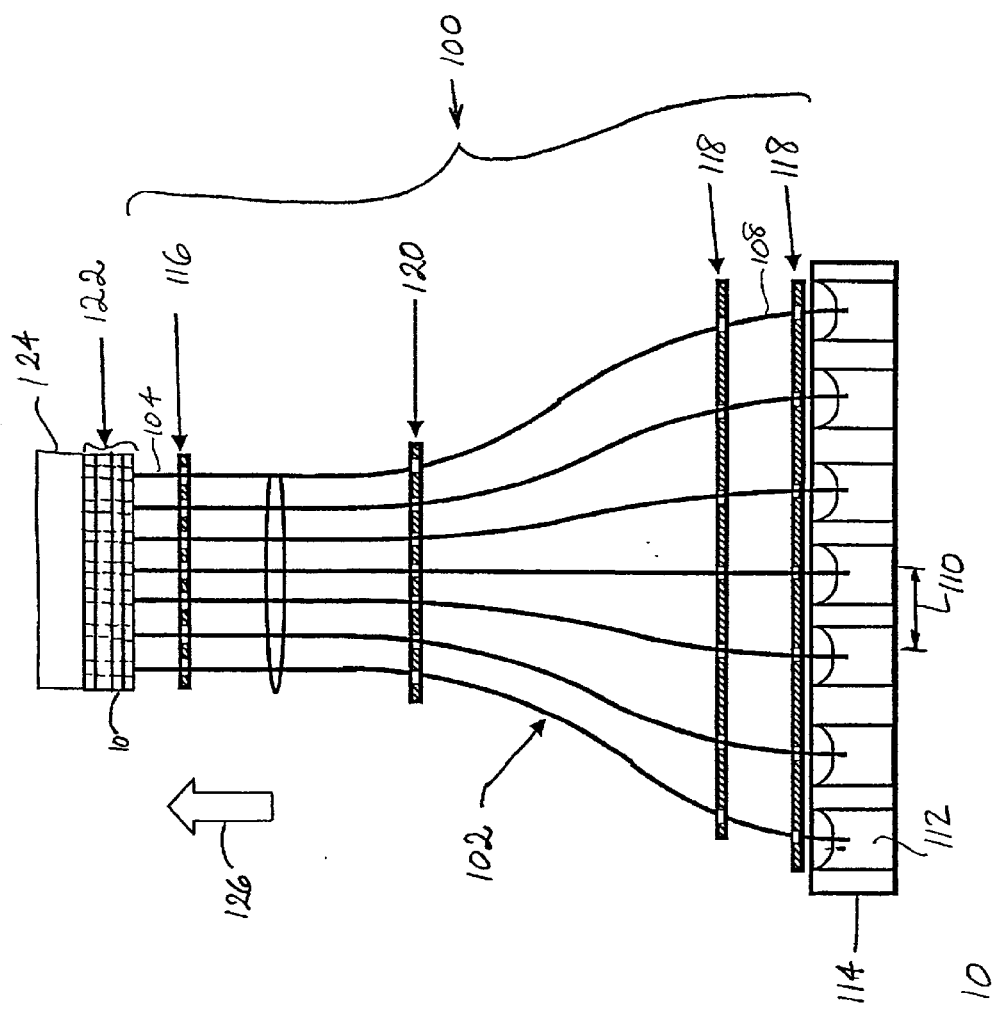
FIG. 10 is a schematic depiction of a method for sampling the contents of a large-format microtiter plate and loading a subarray of the through-hole array in accordance with an embodiment of the present invention.
Figure 11:
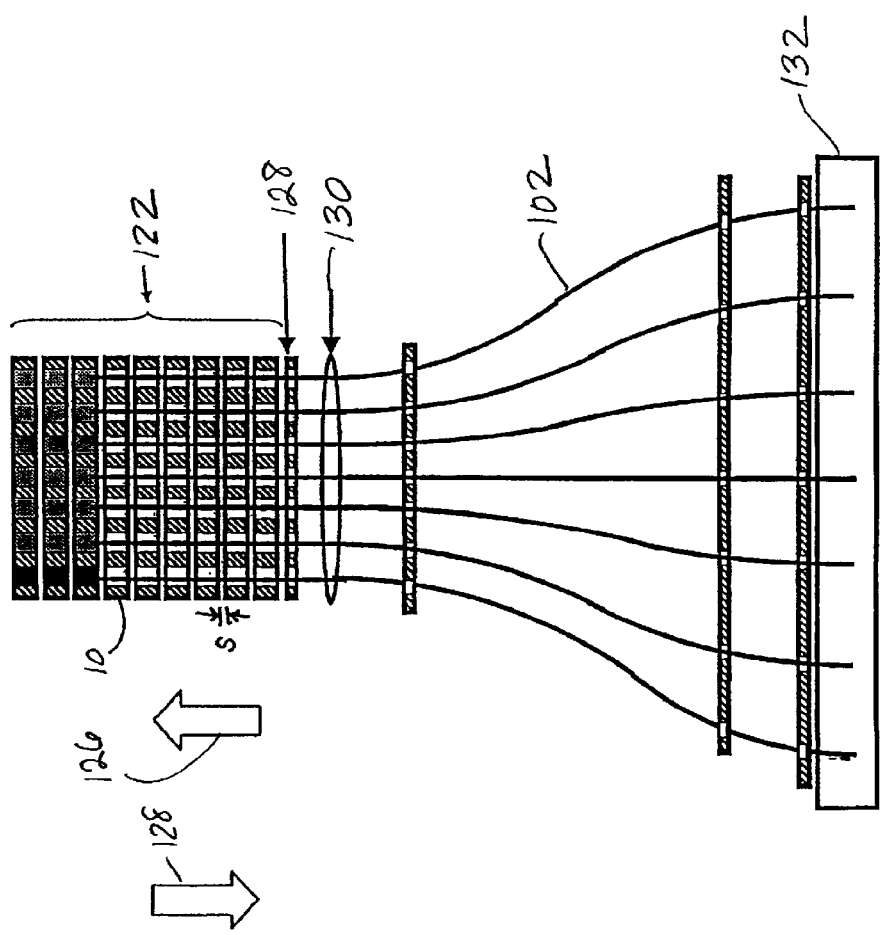
FIG. 11 is a schematic depiction of a method for sampling the contents of a large-format microtiter plate and loading subarrays of multiple through-hole arrays in accordance with an embodiment of the present invention.

Referring now to FIGS. 10 and 11, further embodiments of the invention provide an apparatus and methods that are particularly suited to the transfer of liquids from standard microtiter plate formats (such as 96-, 384-,or -1,536-well formats) to a single array of through-holes or multiple, vertically stacked arrays in which holes in the same spatial location from one array to the next are co-registered. Producing such stacks of arrays may be employed advantageously for producing replicates of molecular or cellular libraries.

Capillary Tube Array

Viewed in cross-section, a capillary tube array 100 is constructed from capillary tubing 102 with an external diameter that fits precisely into the through-holes of a through-hole microwell array 10. Tubing array 100 is designed such that tubing 102 at one end 104 has a center-to-center spacing 106 equal to the spacing between holes in through-hole array 10 (or, alternatively, to an integral multiple of the inter-hole spacing) and tubing at the opposite end 108 has a center-to-center spacing equal to the center-to-center spacing 110 of wells 112 in a microtiter plate 114. Plates 116, 118, and 120, with through-holes having these and intermediate separations serve as jigs to hold the tubing in a regular array. Additional through-hole plates 116, 118, and 120 placed between the two ends may advantageously serve as spacer jigs providing additional support for the tubing array as the center-to-center spacing varies over the tubing length.

In addition to filling a single through-hole microwell array 10, the technique depicted in FIG. 10 may be advantageously employed for filling an entire stack 122 of hole-registered microwell arrays. The internal volume of each tube 102 in the capillary array 100 is slightly greater than the total volume of a column of aligned holes in the array stack 122. For example, if the through-hole dimensions in the array are 250 $\mu$m×1000 $\mu$m, giving a volume per through-hole equal to 62.5 nl, then the volume of one set of holes in a stack of 100 arrays is 6.25 $\mu$l (100×. 62.5 nl). Capillary tubing with an internal diameter of 200 $\mu$m and an external diameter of 245 $\mu$m is readily available; thus a minimum tube length of 200 mm stores the volume of fluid needed to fill this set of through-holes.

One end 108 of tubing array 100 is inserted into the wells of a microtiter plate 114, each tube being inserted into a corresponding well 112. Next, a negative pressure difference is applied across the length of tubing 102 to draw liquid, in direction 126, from each well into its corresponding tube. Negative pressure could be applied to each tube individually, or as shown in FIG. 10, the ends of the tube array can terminate in a chamber 124 that can be partially evacuated. After filing each tube of the array, the microtiter plate 114 is removed. The liquid can be stored in the tubing array for an indefinite period of time, either frozen or in a humidified environment. It can also be readily transported to another location in this format. Multiple tubing arrays can be filled from the same microtiter plate (assuming there is sufficient volume of liquid per well) or different tubing arrays can be filled from different microtiter plates.

Proximity Filling

Embodiments of the invention also provide for methods for filling a stack of arrays, as shown in cross-section in FIG. 11, by bringing the end of a tubing array 130 into close proximity with a matching set of through-holes in the array stack 122. The tubing array can be aligned relative to the array stack by an alignment plate 128 with through-holes having the same center-to-center spacing as the through-holes into which fluid is placed. Each array 10 in the stack 122 is spaced a small distance s that may be, but is not limited to, an equal distance to the through-hole spacing. Application of pressure to the end of the tubing array, placed inside a pressurized container 132, forces fluid from each capillary tube 102 into the opposing through-hole. After the through-hole is filled, a liquid drop can begin to grow in the space between the two plates. When the drop reaches a size that it contacts the through-hole in the plate above it, surface tension draws some fluid into the through-hole. Once the fluidic bridge is established, liquid can flow into the through-hole, driven by the constant pressure applied to the opposite end of the tubing array. With no applied pressure, the drop retreats into the through-hole, the fluidic bridge between each plate is broken, and the separation of array plates after filling can be facilitated (i.e., because there is generally no surface tension that needs to be overcome). Successive filled plates 10 are then withdrawn, and the tube array may be retracted in direction 128. Each vertically registered set of through-holes may thus act as a channel for fluid flow. The hydrophobic coatings on the exterior surface of the arrays prevent liquid from flowing into adjacent holes. This technique can also advantageously be used to create replica plates of a cell library by applying a cell suspension with a pressure uniformly to the array stack.

Inter-hole Spacing Matched to a Microtiter Plate

Figure 12A:
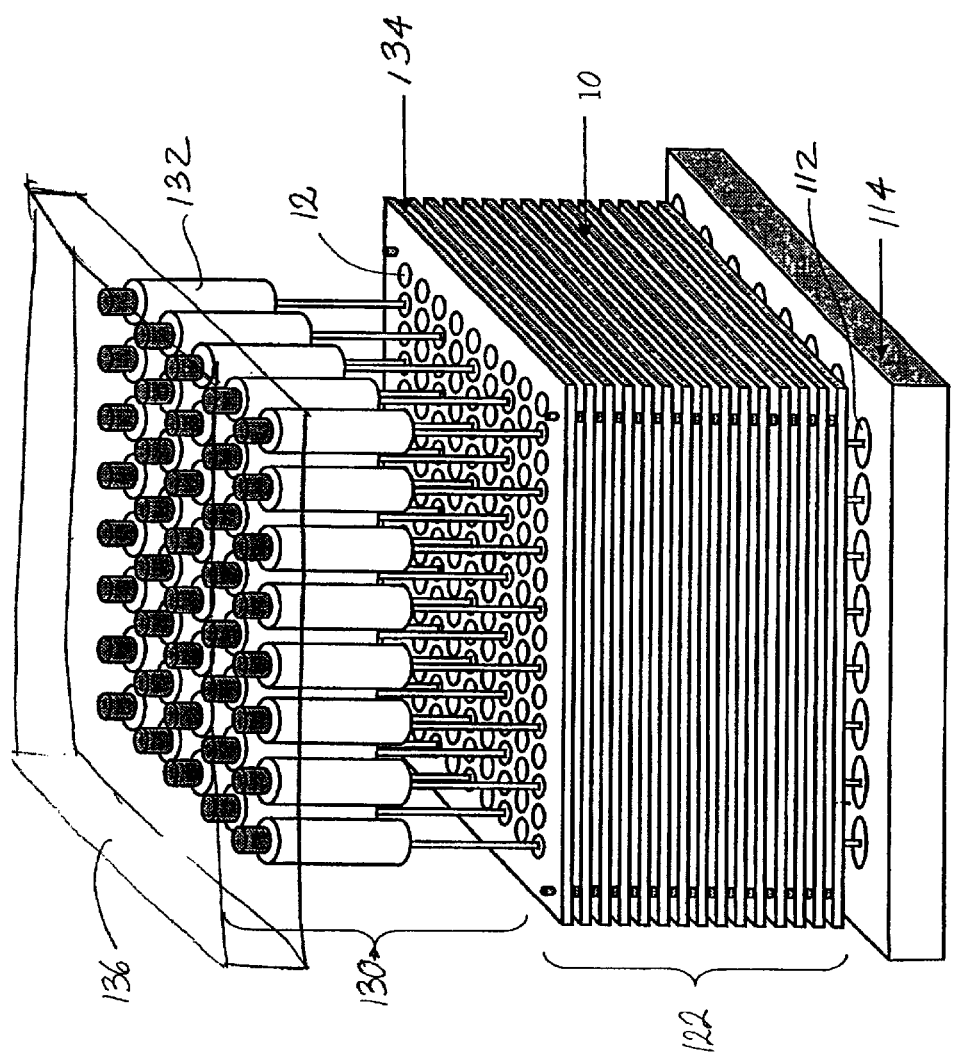
FIG. 12a depicts parallel loading of subarrays of multiple stacked microwell arrays in accordance with embodiments of the present invention.

A method for filling a through-hole array stack, in accordance with alternate embodiments of the invention, is shown in FIG. 12. This method uses a through-hole array 10 having the same lateral dimensions as a microtiter plate 114 and having a hole spacing that is an integral fraction of the well spacing in the microtiter plate 114. When the array is placed on top of the plate, one or more through-holes 12 align with respect to each well 112 in microtiter plate 114. An array 130 of syringes 132 with a center-to-center spacing equal to the well spacing can thus be positioned over a stack of through-holes registered with respect to each other and the microtiter plate. The syringe array is inserted through a through-hole plate 134, such that the plate is a mechanical guide for the syringe tubing as it is moved relative to the array stack. The syringe plungers are mechanically coupled and actuated by a mechanical or electromechanical driver module 136, such that liquid is drawn into or expelled from each syringe in parallel. The syringe tubing outside diameter is preferably sized relative to the through-hole lateral dimensions to give a sliding fit, and the tubing can have a length suitable to allow insertion through the array stack 122 and into the liquid contained in the microtiter plate wells 112.

The volume of liquid withdrawn into each syringe preferably equals the volume of liquid in a column of aligned through-holes in the array stack. The liquid can then be dispensed as the syringe array is retracted from the array stack, and the rate of dispensing can be synchronized with the rate of withdrawal, such that each through-hole addressed by the syringe array is filled. Once this operation is completed, either a new set of holes in the array stack can be filled from the same microtiter plate or the syringe array can be washed and different set of holes filled from a different microtiter plate.

All of the filling examples given above may be performed in parallel on a single array stack with multiple capillary tubing arrays filled with liquids from different microfiter plates or the same microfiter plate. The time to transfer fluid from chemical libraries stored in 96 and 384 well microtiter plates with these methods can be quite rapid. Assuming, for example, that 100 arrays with 10,000 through-holes per array are to be filled with liquid stored in 96 well plates, and that each transfer operation (plate exchange, fluid loading and transfer) takes approximately 20 seconds, then it would take approximately six hours to fill all of the arrays. The filling operations can take place in an environmental controlled chamber (temperature, humidity, atmosphere, etc.). The invention also provides a method for screening compound libraries to predict the ability of each compound to be absorbed by a patient.

Transfer from a Microtiter Plate with an Array of Flexible Members

Figure 12C:
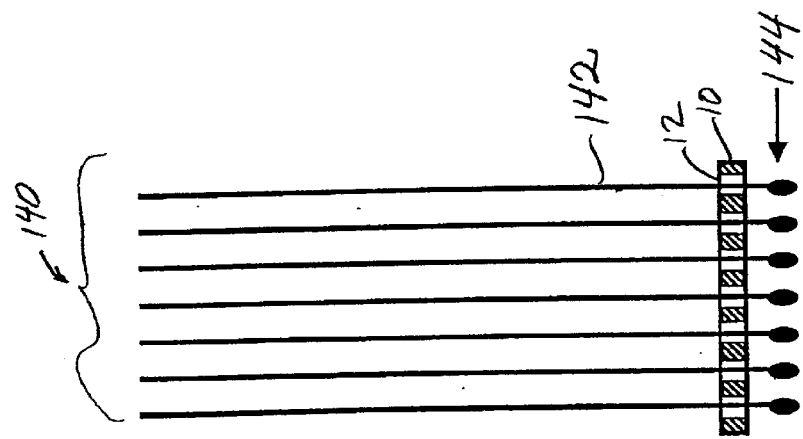
FIGS. 12b and 12c depict parallel loading of subarrays of a microwell array by means of flexible members, in accordance with embodiments of the present invention.
Figure 12B:
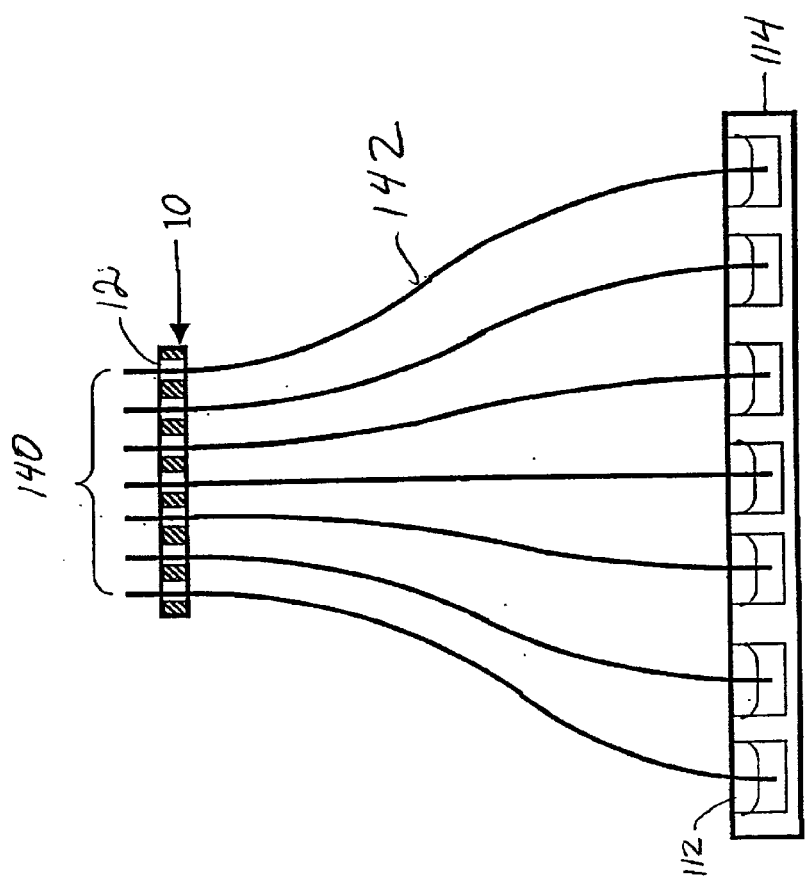

As now described with reference to FIGS. 12*b* and 12*c*, fluid can be transferred from individual wells 112 of a microtiter plate 114 with an array 140 of flexible members 142, e.g., shape memory alloy fibers. The fiber diameter is equal to or less than the inside dimension of the through-holes 12 in the array 10 into which fluid will be transferred. The number of fibers in the bundle may, for example, be equal to the number of wells in the microtiter plate 114. The ends of the fibers at one end of the bundle can have a center-to-center spacing equal to the spacing of the holes in the through-hole array, while the ends of the fibers at the opposite end can have a center-to-center spacing equal to the spacing of wells in the microtiter plate. The fibers can be held in place with a series of through-hole jigs designed to increase the spacing between fibers from one end of the bundle to another. Once fixed in place, shape memory alloy fibers can be heated above their critical transition temperature to make the imposed fiber curvature permanent. After they are cooled to room temperature, the fibers can be removed from the holding jig, with the change in fiber center-to-center spacing intact. The close packed end of the fiber bundle can then be inserted into the through-hole array into which fluid from each well in the plate is to be placed. The opposite end can be arranged such that each fiber is positioned above a well in the microtiter plate, and the ends of the fibers can be immersed in the fluid contained in each well. On retraction of the fiber bundle from the microtiter plate, as shown in FIG. 12*c*, a small volume drop 144 remains attached (e.g., by surface tension) to the end of each fiber 142. A force may be applied to the opposite end of the fiber bundle to pull the bundle through the holes 12 of the through-hole array 10, such that the fluid is brought into contact with the corresponding through-holes. As the fibers 142 are pulled through the hole 12, surface tension acts to hold the liquid in the through-hole as the fiber is removed.

Successive Dilution

Figure 13A:
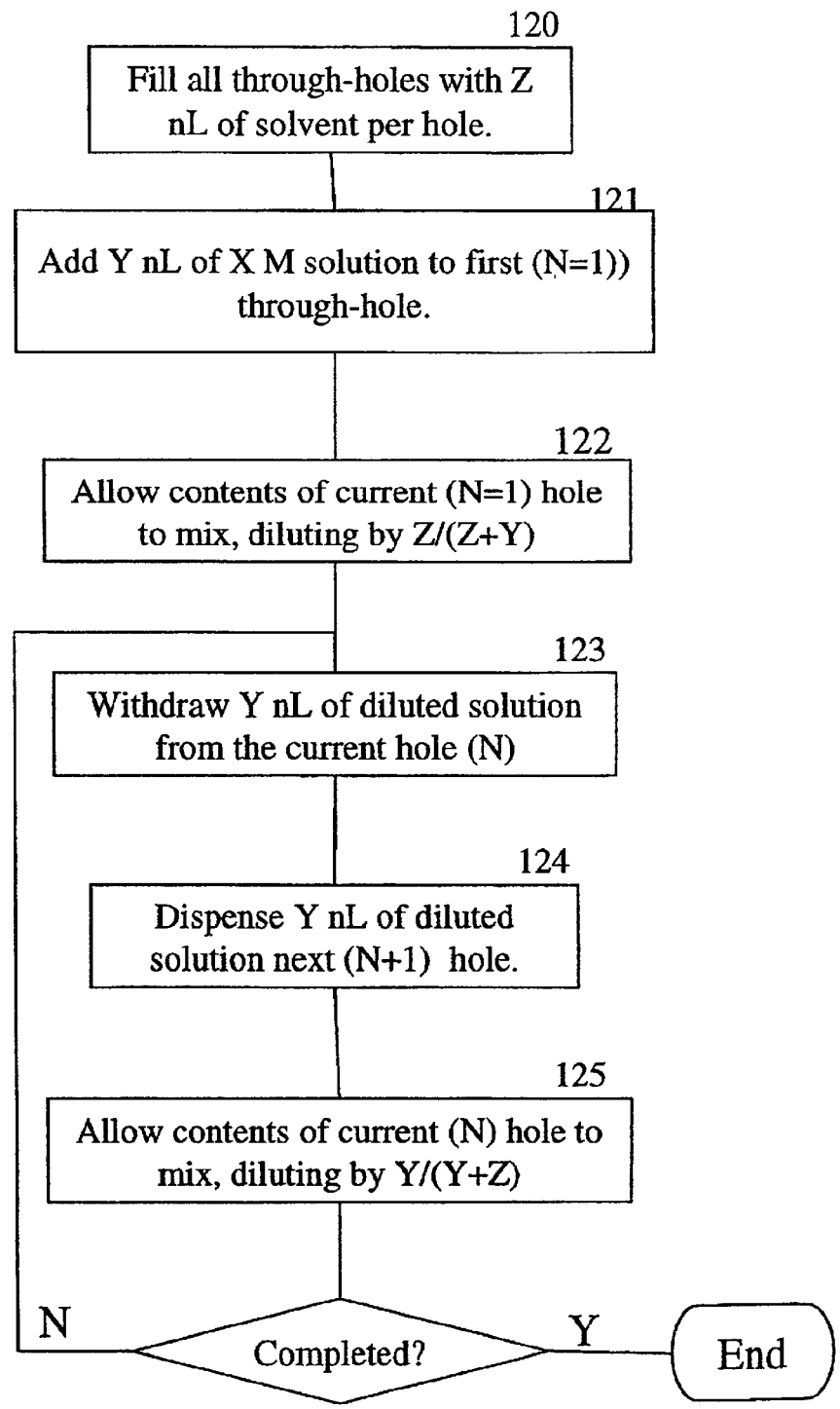
FIG. 13a is a flow chart depicting a method for successive dilution of the contents of a microwell array in accordance with an embodiment of the present invention.

Addressable loading may also be employed to fill a series of through-holes with different and specified concentrations of the same solute. A chosen series of through-holes is filled with a quantity of solvent, denoted Z nanoliters (nL), either by dipping the holes into the solvent or by dispensing the solvent from a microsyringe 232 (shown in FIG. 21), or other fluid transfer device. This is shown as the first step 120 in the flow chart of FIG. 13. In step 121, microsyringe 232, or another fluid transfer device, is filled with an X molar solution of the solute, and is then positioned over the first through-hole. Y nL of this solution, where (Y+Z) nL is sufficient volume to overfill the hole and to create positive menisci, is expelled such that it forms a droplet at the end of the syringe tip. The syringe tip is lowered until the solvent droplet contacts the surface of the solution, causing the two liquids to mix 122 and produce a solution of concentration YX/(Y+Z) molar. The outer surface of the syringe tip and the faces of the array must be nonwetting toward the solution being dispensed. The syringe plunger is then withdrawn in step 123 to suck up Y nL of the diluted solution. The syringe tip is positioned above the next (N+1) through-hole 124 and Y nL of the diluted solution is dispensed into the solvent to dilute 125 by another factor of Y/(Y+Z). The process is repeated so as to dispense solution into a series of individual through-holes, each time diluting by Y/(Y+Z).

Chemical Gradient Methods

In accordance with preferred embodiments of the invention, a particular chemical species is not loaded uniformly into all the holes of an array, but, rather, a gradient of chemical species is created in at least one dimension in a two-dimensional through-hole array. As used in this description and in any of the appended claims, the term "gradient" refers to its ordinary mathematical meaning, i.e., a variation, along one or more directions, of a specified quantity. The directions, here, are taken along the surface of an array of through-holes. Thus, a gradient in the concentration of a specified chemical species in the through-holes may be said to exist with respect to a particular direction, or, for that matter, with respect to various directions. Thus, a particular gradient may be, but need not be, monotonic, and the concentration of a species, in a specified direction, may rise and fall.

Referring now to FIGS. 9*a*–9*c* and 14*a*–14*c*, dip loading methods described above may be used for creating a concentration gradient in an array of through-holes. In accordance with such methods, the array is dipped into a chemical solution at a controlled rate such that the chemicals in the solution have different amounts of time to mix with, or react with, substances by diffusion into various through-holes.

Figure 14C:
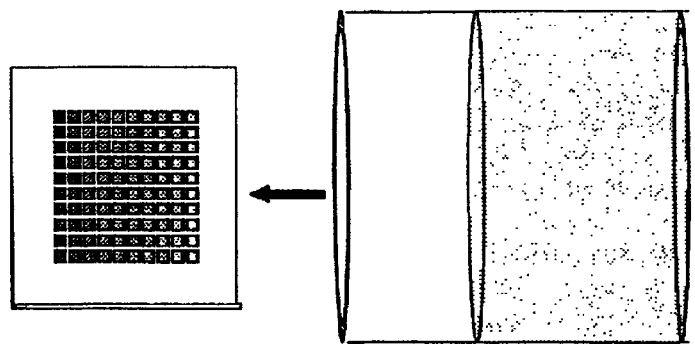
FIGS. 14a–14c depict a sequence of operations for exposing respective through-holes of a through-hole array to a second liquid and for creating a specified gradient of a specified characteristic with respect to placement of the through-holes in the array in accordance with an embodiment of the present invention.
Figure 14B:
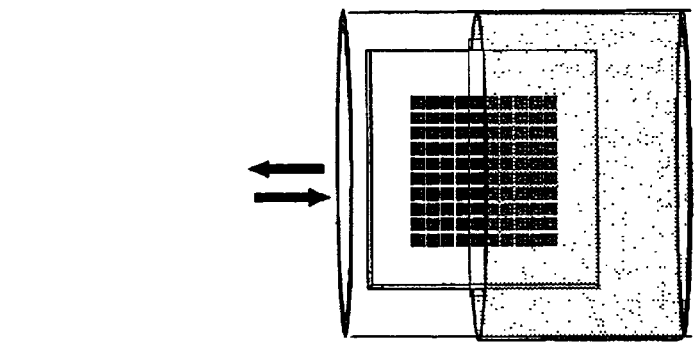
Figure 14A:
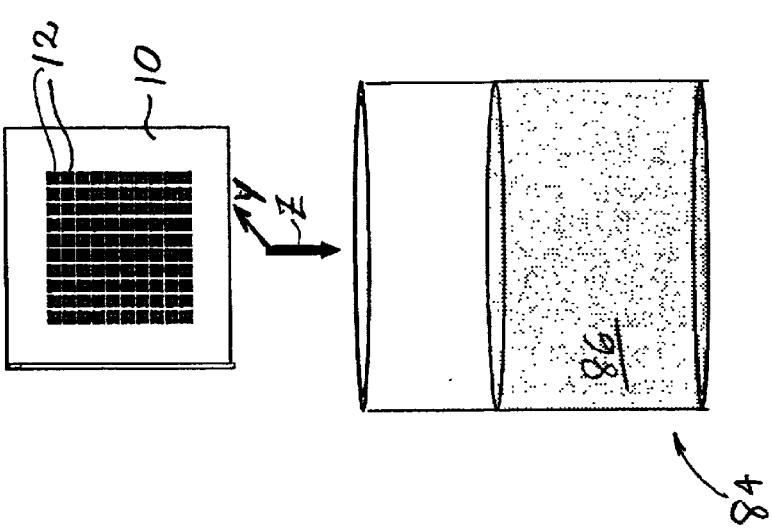

After an array has been filled, by dip loading, with first liquid 82, as discussed above with reference to FIGS. 9*a*–9*c*, plate 10 is subsequently lowered into a second container 84 containing a second liquid 86, as shown in FIG. 14*a*. Since the through-holes of plate 10 are now filled with the first liquid 84, the second liquid 86 may diffuse into, mix with, displace, or otherwise react with, the contents of through-holes 12. Each of these processes is characterized by a rate. Instead of fully immersing the plate until the particular reaction, physical or chemical, runs to completion, plate 10 may be partially immersed into second liquid 86, as shown in FIG. 14*b*, for a specified duration of time, and then withdrawn, wholly or partially, as shown in FIG. 14*c*. If plate 10 is reimmersed in liquid 86, to a different depth 88 and for a newly specified duration of time, certain of the through-holes 12 will contain material subject to differential physical or chemical processes. Thus, a gradient will have been created with respect to the direction z along the array of through-holes. Naturally, this process may be repeated or otherwise modified to create a specified gradient.

Figure 14D:
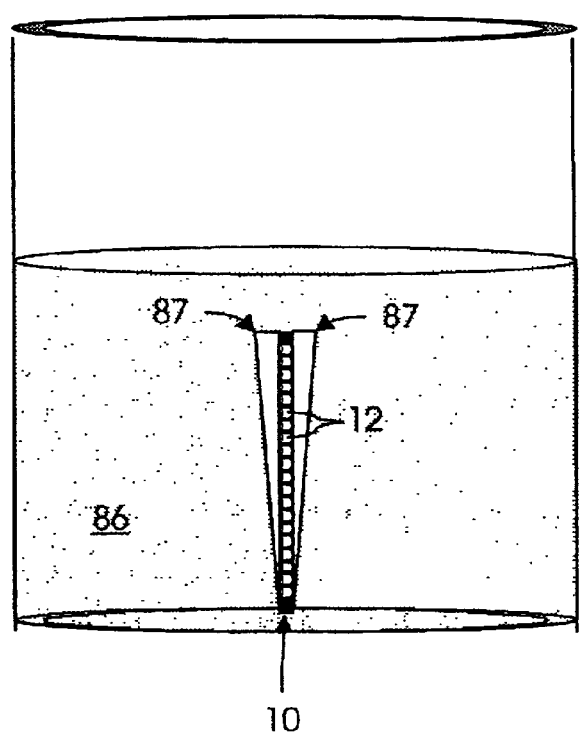
FIG. 14d shows a side view is shown of a through-hole array plate with a graduated filter for providing a concentration gradient in accordance with an embodiment of the invention.

In accordance with alternate embodiments of the invention, other means may be employed in order to spatially modulate the concentration of a specified species allowed to diffuse into a through-hole located at a particular position within the array. Referring to FIG. 14d, a side view is shown of through-hole array plate 10 immersed in liquid 86. Diffusion of liquid 86 into through-holes 12 is modulated by membrane or filter 87, for example, that, by virtue of its tapered shape or otherwise, gives rise to a gradient of a specified species with respect to the position of a through-hole within the array.

In a related example, by slowly lowering a through-hole array filled with a gel forming solution thin-edge first into a polymerization initiating mixture different gel densities may be obtained within in holes. By rotating plate 10 by 90° about axis y transverse to the surface of the plate, and then slowly dipping into a reagent that derivatizes the gel with a free cationic moiety, and then rotating another 180° about y and slowly dipping into a reagent that derivatizes the gel with an anionic moiety, a two-dimensional size/charge selection matrix is created that is useful for separating protein mixtures in a manner similar to a 2-D polyacrylamide gel, but with the advantage of greater separation speed and greater access to the separated proteins.

Figure 15:
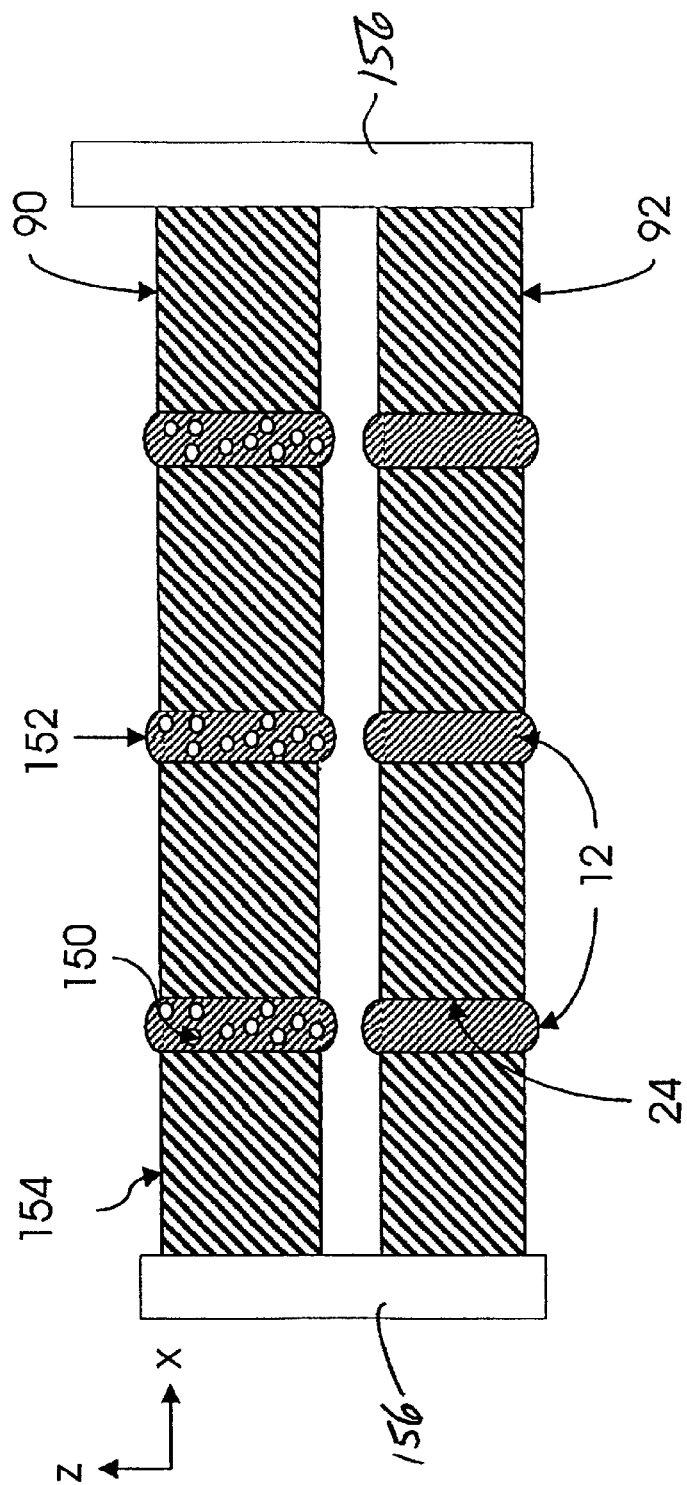
FIG. 15 depicts mixing of the contents of a through-hole array with the contents of another through-hole array brought into registration of the through-holes in accordance with embodiments of the present invention.

In another embodiment, concentration gradients within through-hole arrays are use to optimize the concentrations of A and B in a two-component reaction between Reagent A and Reagent B. The mixing process is described in greater detail below. Referring to FIG. 15, a first through-hole array, shown in cross section and designated generally by numeral 90, is loaded with Reagent A using a chemical gradient method that results in the through-holes along one row, in the x direction, of the array will have the same concentration of A and the concentration gradient is along the array columns, in the z direction. A second array, designated generally by numeral 92, is loaded with Reagent B such that the concentration gradient is along the rows (x direction) of the array and through-holes along a column (z direction) of the array have all the same concentration. Bringing the two arrays in contact causes mixing between aligned through-holes 12. Along each row or column of the combined arrays the concentration of A relative to B in the mixture changes in a regular and known manner. Along the array diagonal, the concentrations of A and B in the mixed liquids are equal and but changing in overall concentration.

Variants from the basic scheme for creating a known two-dimensional gradient in the relative proportions of A and B include loading the A and B arrays by dipping along a diagonal, by the orthogonal combination of two arrays each with a 2-D gradient of A relative to B or by dilution with arrays loaded with Reagent A or B where some of the through-holes are empty. Analysis of the through-hole contents readily determines optimal reaction conditions since the reaction conditions in each through-hole are known. Gradients created in the solution with respect to quantities other than solute concentration are also to be understood to be within the scope of the present invention, and may include, without limitation, such characteristics as temperature, electric field, magnetic field, etc.

Mixing and Dilution

As discussed in greater detail in the following sections, microwell plates may advantageously be stacked for such purposes as mixing or dilution. One such application is the apportionment among through-holes of a sample of cells. Considering, for purposes of example only, through-holes on a single plate that are 250 $\mu$m square and 500 $\mu$m deep. When three such microchannel plates are stacked (as would be the case in a 2-step assay), the total volume of a single channel (i.e., the combined volume of three through-holes) is ~100 nL. If the entire channel is filled from a dense yeast cell culture (~$10^7$/mL) each channel then contains approximately $10^3$ yeast cells. Based upon a yeast cell volume of 70 $\mu$m$^3$, the maximum number of cells per 100 nL channel is on the order of $10^6$, consonant with a typical minimum of 100 cells per microchannel is required to compensate for variable yeast cell response to the bioassays.

Referring to FIGS. 15–19, mixing and dilution are shown between the contents of two substantially planar through-holes array plates 90, 92 (i.e., array plates having neither flanges nor indentations). In FIG. 15, in particular, a cross-sectional view is shown of portions of two through-hole arrays 90, 92. Both the top and bottom surfaces of each platen are hydrophobic, as discussed in detail above. The through-hole walls 24 are preferably hydrophilic. Through-holes 12 of both platens are overfilled with high surface energy fluids 150, such as aqueous solutions, for example, such that each through-hole 12 has a positively-curved meniscus 152 protruding above the platen surface 154.

Alternatively, the platen surfaces 154 may be hydrophilic and a sufficient amount of a low surface energy fluid, such as an alkane, for example, is loaded into the through-holes 12 to form positive menisci 152.

Figure 16:
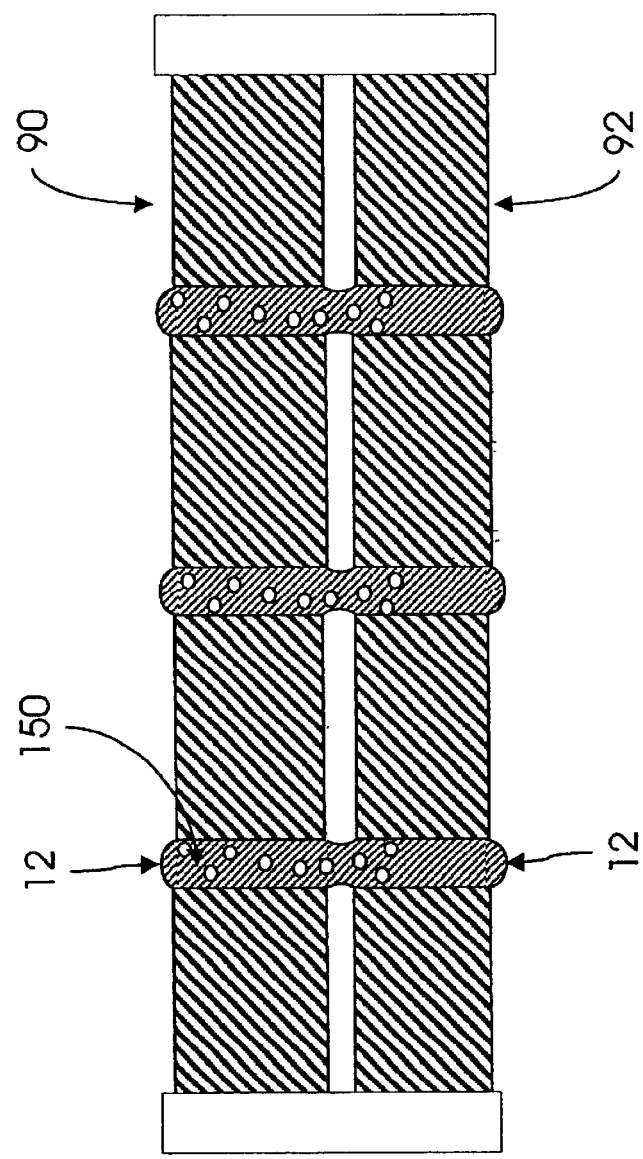
FIGS. 16 and 17 depict further stages in the mixing of the contents of a through-hole array with the contents of another through-hole array brought into registration of the through-holes in accordance with embodiments of the present invention.
Figure 17:
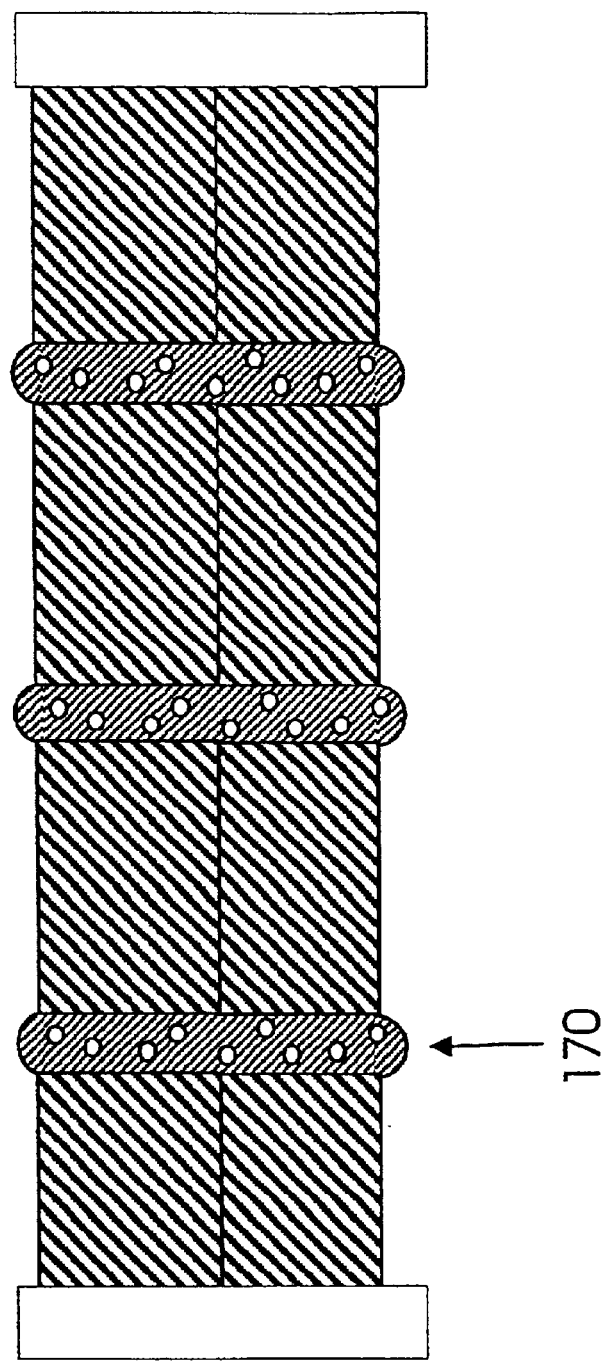

FIG. 16 shows a cross-sectional view of the two platens 90, 92 after the surfaces of the liquids 150 in co-registered through-holes 12 are brought into contact. The release of the surface tension drives convective mixing between fluids contained in the opposite platens 90, 92. Once the two surfaces of the platens themselves have been brought into contact, each set of two-coregistered through-holes forms a longer channel 170, as shown in FIG. 17. Mixing proceeds within the longer channels by a combination of convection and statistical diffusion.

Figure 18:
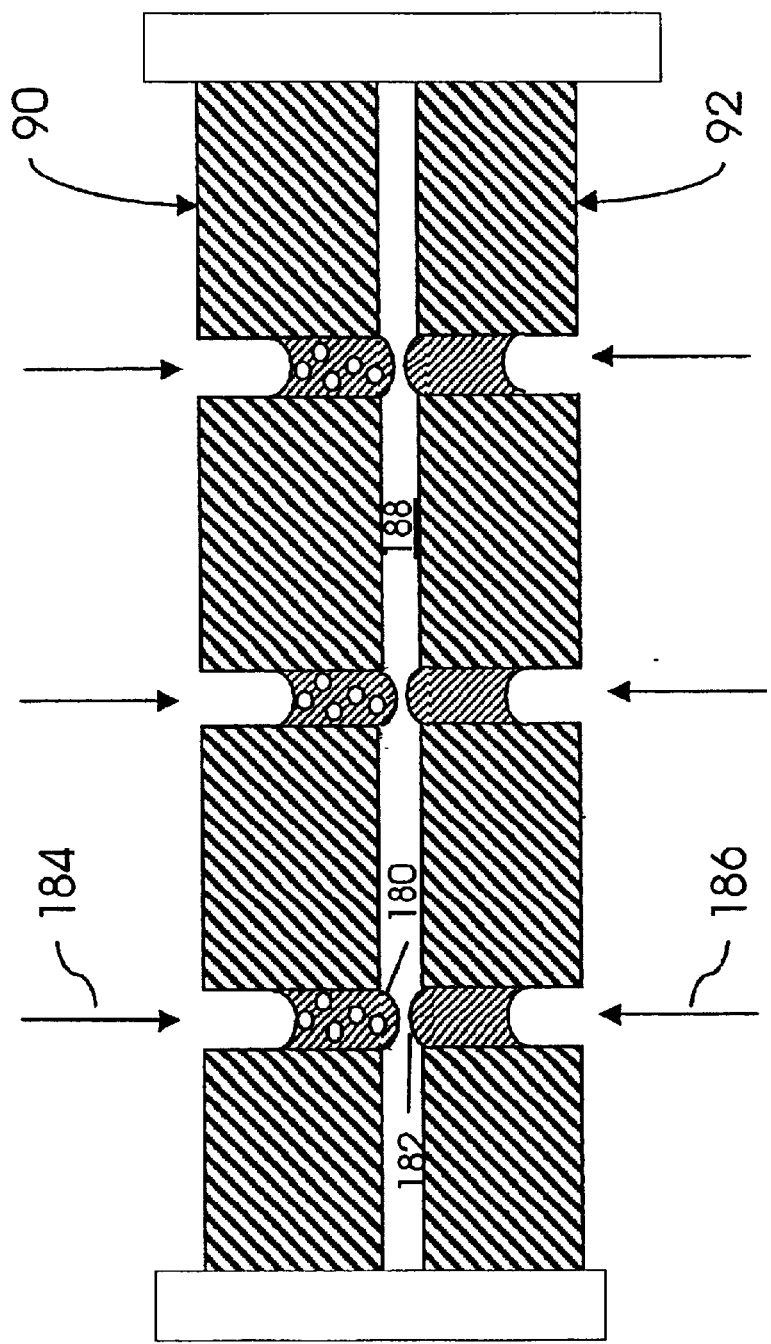
FIG. 18 depicts mixing of the contents of a through-hole array with the contents of another through-hole array by application of external pressure, in accordance with embodiments of the present invention.

Referring to FIG. 18, in cases where through-holes 12 of one or both of arrays 90, 92 are underfilled (such that there is an air-gap separating the fluid 180, 182 when the plates are contacted), the application of slight positive pressure, designated by arrows 184, may be employed to bring the surfaces of the two fluids into contact while a small gap 188 is still present between the surfaces of the two platens 90, 92.

Figure 19:
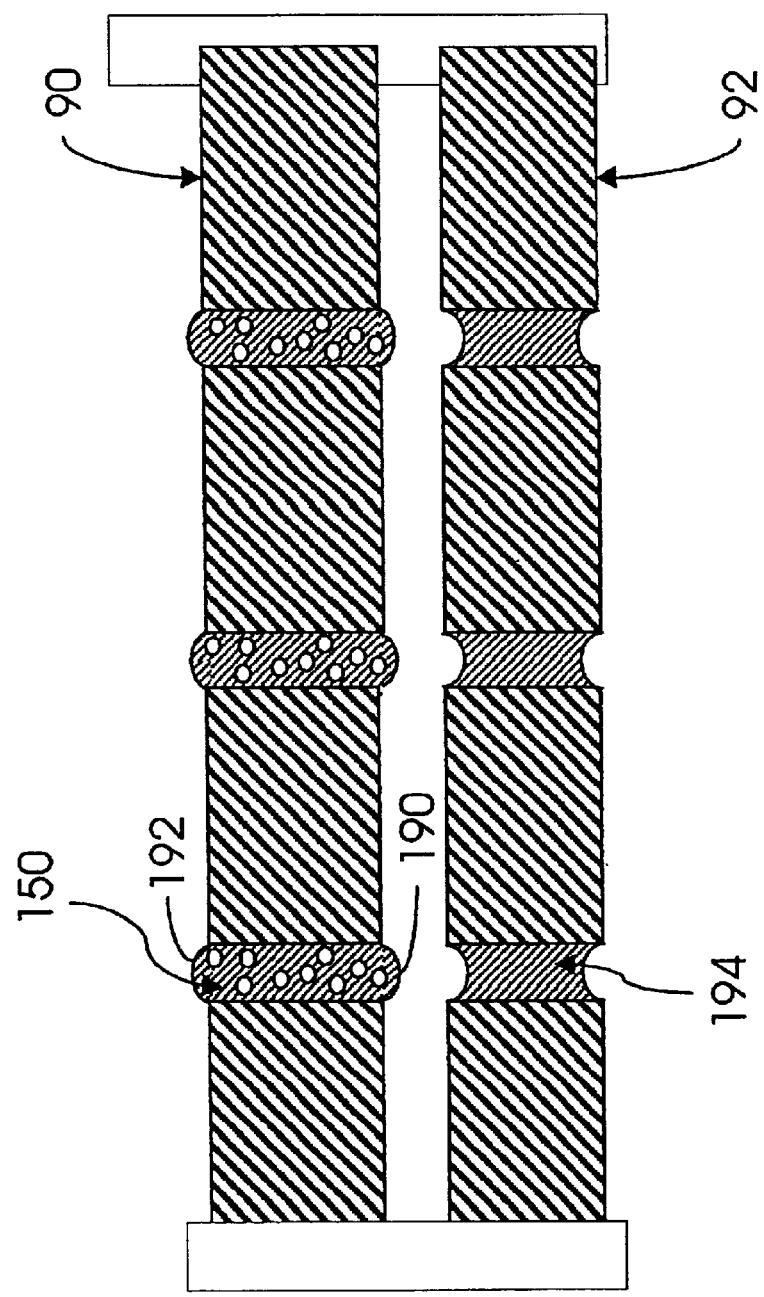
FIG. 19 depicts mixing of the contents of a fully filled through-hole array with the contents of another incompletely filled through-hole array brought into registration of the through-holes in accordance with embodiments of the present invention.

In yet other embodiments of the invention, with reference to FIG. 19, first platen 90 is filled with sufficient fluid 150 to form positive menisci 190, 192, while a second platen 92 is filled with an amount of fluid 194 that is insufficient to form positive menisci, but sufficient to make contact with the surface 190 of the menisci of the first platen when the two platens are stacked. Mixing proceeds by bringing the liquid surfaces into contact as previously described.

Control of Environmental Factors

Figure 20:
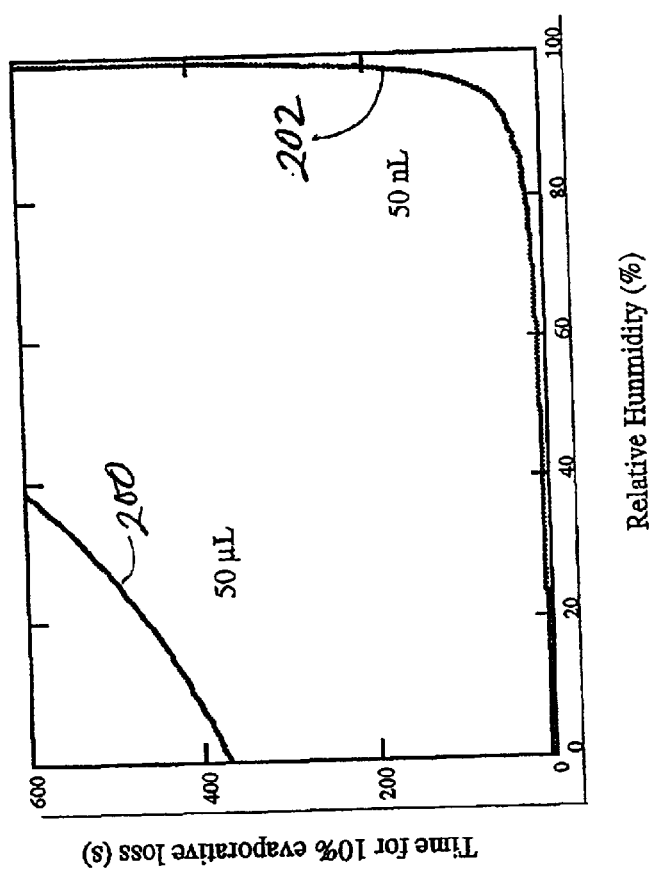
FIG. 20 shows plots of calculated times for evaporation of a water droplet as a function of the ambient relative humidity.

In accordance with embodiments of the invention, methods and apparatus are provided for maintaining high relative humidity levels (typically above 95%) in the environment surrounding through-hole arrays during various operations of the invention. Maintenance of high humidity levels may advantageously minimize, if not eliminate, evaporation of solutions contained in the through-hole arrays. The level of humidity required to keep the volume loss at an acceptable level depends upon the length of time needed to perform the various desired operations, as well as on such factors as the ambient temperature, and the volume of fluid contained in each through-hole. At a temperature of 21° C., the evaporative loss expected from a droplet of water may be predicted in accordance with Fick's law, as depicted in FIG. 20. The time, in seconds, for 10% evaporative loss is plotted for a 50 µL droplet (by curve 200) and for a 50 nL droplet (curve 202) as a function of relative humidity. Unless humidity levels are close to 100%, the smaller droplet will evaporate very rapidly, with a 10% mass loss in 11 seconds at 65% relative humidity.

Humidity Control during Addressable Loading and Unloading

Figure 21:
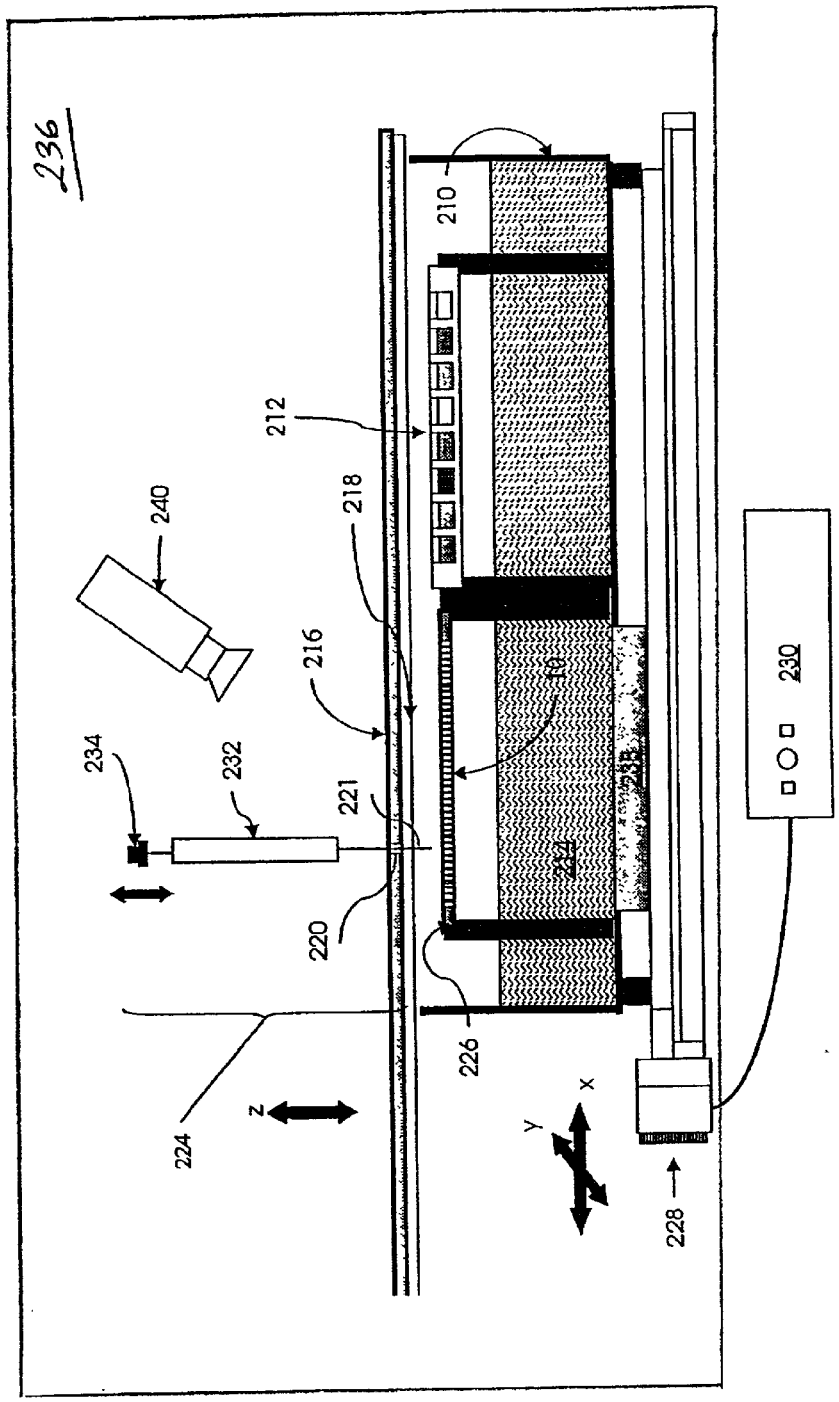
FIG. 21 depicts a humidity chamber for loading and unloading through-holes while maintaining a high relative humidity in the environment surrounding the array, in accordance with an embodiment of the present invention.

With reference to FIG. 21, and apparatus is provided for advantageously reducing the volume of the enclosed environment subject to humidity control. In accordance with embodiments of the invention, a through-hole array 10 is mounted above a reservoir 210 of water. A 96-well, 384-well or higher density microtiter plate 212 is mounted above the same reservoir proximal to the through-hole array. Reservoir 210 may contain a water absorbent material such as a sponge 214 to keep the water from sloshing when the reservoir is moved. An optically transparent plate 216 is placed on top of the reservoir separated from the walls of the reservoir by a thin layer 218 of a viscous non-hydroscopic fluid such as silicone grease, for example. One or more small holes 220 are drilled through transparent plate 216. Through each hole a microsyringe needle 222, microcapillary, pin, cannula, or other fluid transfer element is inserted.

Computer control of motorized translation stages may be provided, such as along axis y to move the fluid transfer element 224 towards and away from the top face 226 of the through-hole array 10. Fluid transfer element 224 may include syringe 232 with plunger 234 fluid transfer element 224, for example. Additionally, the arrays and reservoir may be moved in the plane of the x and y axes, preferably by motorized stage 228 under control of controller 230, with respect to the fluid transfer element. If indicated, further computer-controlled stages may be provided, for example, to actuate the fluid transfer device. Transfer of materials between the microtiter plate and through-hole array proceed by means described above in reference to FIGS. 10–12.

Additional reservoir(s) containing solution(s) for cleaning/sterilizing the fluid transfer element may also be provided within the confines of chamber 236 which encloses the apparatus heretofore described. Alternatively the water in the large reservoir 210 may be used for this purpose. An illumination source 238 may also be provided for to illuminate the array for optical inspection during loading/unloading, either visually or by means of a video camera 240.

Humidity Control During Dip Loading and Mixing

An environment enclosure 236, as shown in FIG. 21, may also be utilized in order to preventing evaporation from the through-hole arrays during dip loading and mixing. Sealable chamber 236 is large enough to contain the array and necessary apparatus for performing such desired operations as are required, including, for example, motors and translation stages 228, as well as an alignment jig 156 (shown in FIG. 15) for mixing operations.

Cool water vapor is generated by an external humidifier and injected into the chamber through a port. An ultrasonic humidifier is able to generate enough vapor to maintain humidity levels above 95% in a 0.13 cubic meter chamber. A circulation system consisting of a fan and baffles is provided to distribute the water vapor uniformly throughout the chamber. Various doors, hatches and iris ports may be provided for accessing the interior of the chamber. The temperature within the box may be controlled by a resistive heater and an electronic temperature controller. Such a chamber may be assembled by attaching a second humidifier to a commercial infant incubator.

Any surface which must be kept dry, including optical windows, and corrodible metals may be heated slightly above the ambient to prevent condensation. A humidity sensor is also provided to monitor humidity levels inside the chamber. All computer and electronic hardware are placed outside the chamber and are connected to components inside the chamber via a wire feedthrough.

The through-hole array may be filled within the chamber, or loaded externally and transferred into to the chamber in a humidified sealed cassette.

Humidity Control during Optical Analysis and Transfer between Loading Stations

Figure 22A:
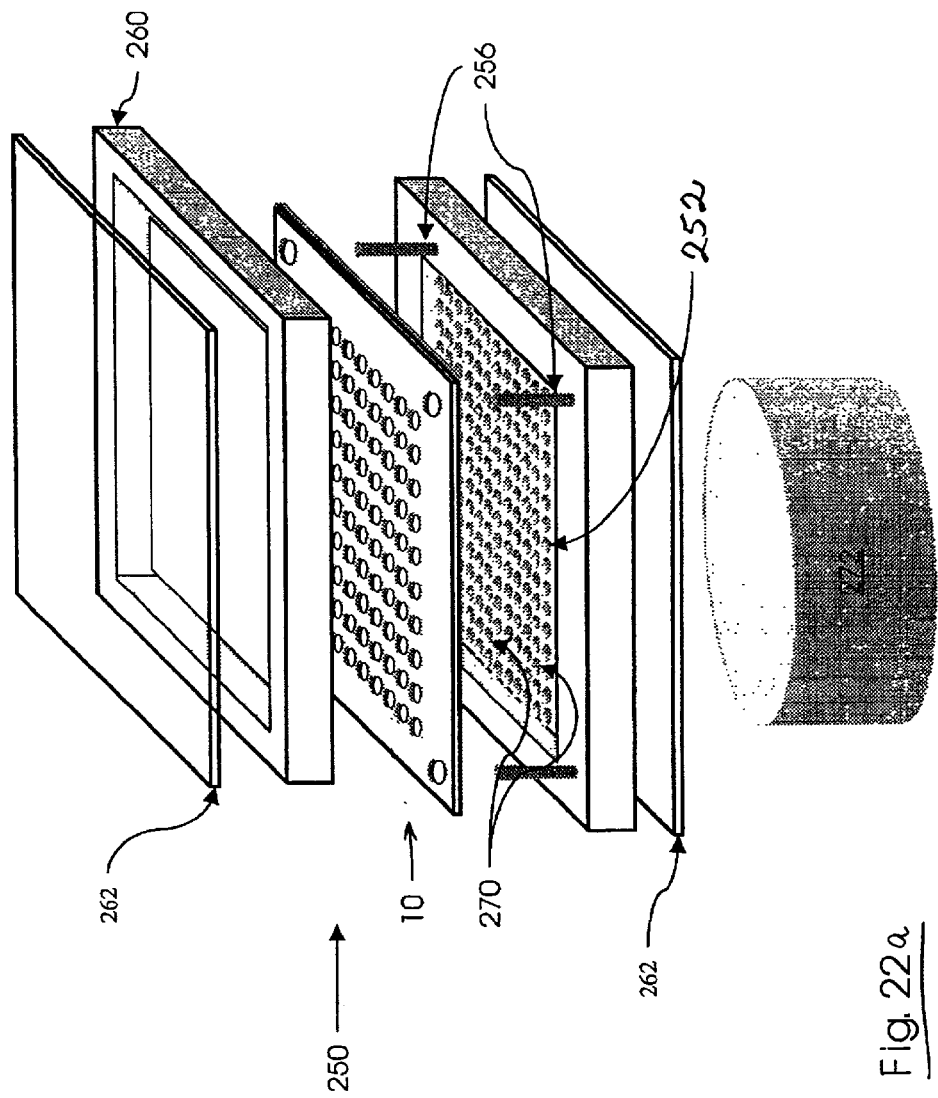
FIG. 22a depicts an exploded perspective view of a portable humidity chamber for preventing evaporation of fluid from the arrays during fluorescent imaging analysis, incubation and transferring the array between other humidified environments.
Figure 22B:
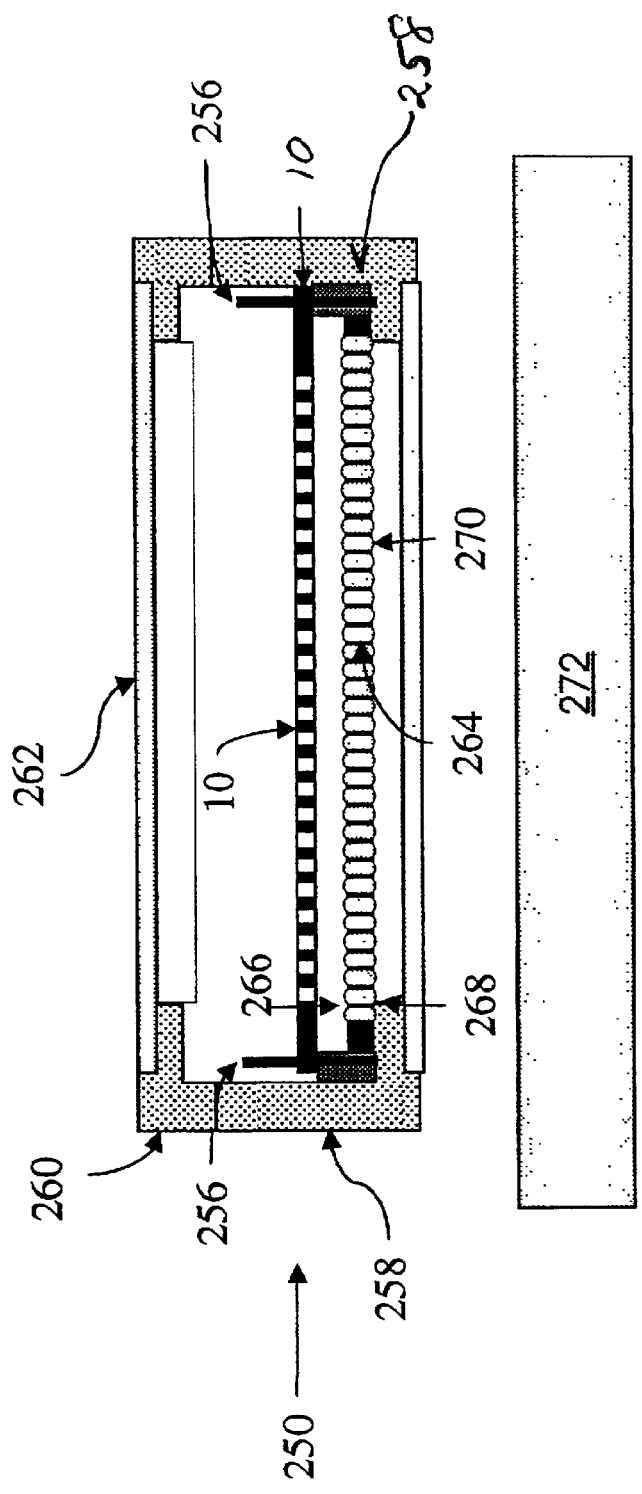

Referring now to FIG. 22a, an exploded perspective view is provided of a compact portable cassette, designated generally by numeral 250, for maintaining relative humidity levels above 95% when the array is removed, for optical analysis, for example, from the humidified loading chamber 236 (shown in FIG. 21). FIG. 22b provides a side view, in cross section, of the humidified cassette 250 of FIG. 22a. Through-hole array 10 and an aqueous microlens array 252 are mounted in a compact, sealable enclosure. The through-hole array is positioned and held in place by means of alignment pins 256 or some other means. Both the array mount 258 and cover holder 260 are covered by an optically transparent plate 262 secured to the mount and cover by adhesive or other mechanical means. The mount may also include magnets, pins, grooves or other physical features to facilitate position the array inside optical analysis equipment.

The humidity is raised by passive evaporation from water contained in a transparent glass microcapillary bundle 252 (or, 'microchannel array') mounted beneath the through-hole array and secured by set screws or some other mechanical means. (Glass microcapillary bundles are manufactured by Schott Fiber Optics, Southbridge, Mass.). Typical dimensions for each capillary 264 are diameter of 200 microns and depth of 1 mm. The top 266 and bottom 268 of the microchannel array 252 are made hydrophobic according to the procedures described above. The arrangement of the capillaries 264 in the array need not be regular. Water 270 in the capillaries forms a set of microlenses which serve to diffuse light from light source 272 across the array and thus provide a uniform illumination field for optical analysis. The use of liquid microlens arrays, generally, is within the scope of the present invention.

Another advantage of the aqueous lens array is that the water is held in place by surface tension. Thus the operator need not keep the humidity cassette level, or avoid applying the typical accelerations that occur when the plate is carried around a room and placed on horizontal surfaces. Also the cassette may be agitated during incubation to promote cell growth inside the arrays.

Control of Other Environmental Factors

Pressure, light and temperature, are controlled by enclosing the array in an appropriately constructed chamber and then controlling the environment inside the chamber by conventional means. To prevent evaporation such chamber must also be equipped to maintain high relative humidity.

Having thus described various illustrative embodiments of the present invention and some of its advantages and optional features, it will be apparent that such embodiments are presented by way of example only and are not by way of limitation. Those skilled in the art could readily devise alternations and improvements on these embodiments, as well as additional embodiments, without departing from the spirit and scope of the invention. All such modifications are within the scope of the invention as claimed.

What is claimed is:

1. A method for loading a plurality of disparate sample containers, the sample containers comprising an integral structure, such that the concentration of a specified substance in each container is characterized by a gradient with respect to position of the container within the structure, the method comprising:
   a. introducing a first liquid into the disparate containers; and
   b. contacting the containers with a second liquid, the second liquid containing the specified substance, in such a manner that the degree of diffusion of the specified substance into the disparate containers differs in a controlled manner among the containers,
   wherein contacting the containers with the second liquid includes differing a duration of contact with the second liquid as among the disparate containers.

2. A method for loading a plurality of disparate sample containers, the sample containers comprising an integral structure, such that the concentration of a specified substance in each container is characterized by a gradient with respect to position of the container within the structure, the method comprising:
   a. introducing a first liquid into the disparate containers; and
   b. contacting the containers with a second liquid, the second liquid containing the specified substance, in such a manner that the degree of diffusion of the specified substance into the disparate containers differs in a controlled manner among the containers,
   wherein contacting the containers with the second liquid includes modulating the diffusion rate of the specified substance into the containers.

3. A method according to claim 2, further comprising the step of creating a gradient of the specified substance in the second liquid prior to contacting the containers with the second liquid.

4. A method according to claim 3, wherein the step of creating a gradient of the specified substance includes applying electrophoresis.

5. A method according to claim 2, wherein the step of modulating the diffusion rate includes contacting the containers with the second liquid through a membrane having a permeability variable with respect to position.

6. A method for loading a liquid into a plurality of through-hole platens, each platen having a plurality of through-holes, the method comprising:
   a. stacking at least two substantially empty platens together in such an adjacent manner that at least one of the plurality of through-holes from each platen is registered with a through-hole of each other adjacent platen so as to form a registration set of through-holes unimpeded by any solid structure; and
   b. transferring the liquid to form a continuous column of liquid in each registration set.

7. A method according to claim 6, wherein each platen is separated from each adjacent platen by an air gap.

8. A method according to claim 6, wherein the step of transferring liquid includes transporting the liquid through capillary tubes.

9. A method according to claim 6, wherein the step of transferring liquid includes transporting the liquid through at least one cannula.

10. A perforated platen having substantially parallel planar surfaces for manipulating distinct liquid samples, each sample having a volume less than 1 microliter, the platen comprising:
   a. an inner layer of hydrophilic material;
   b. two outer layers of hydrophobic material coupled to opposite sides of the inner layer;
   c. a two-dimensional array of through-holes including, at least a first hole having a first liquid, and
   d. at least one hole, adjacent to the first hole, containing a second liquid distinct from the first liquid, the through-holes each having a diameter less than 400 micrometers and a density of at least 1.6 through-holes per square millimeter,
   wherein the two outer layers of hydrophobic material prevent outmigration of the first and second liquids.

* * * * *